US006562363B1

(12) United States Patent
Mantelle et al.

(10) Patent No.: US 6,562,363 B1
(45) Date of Patent: May 13, 2003

(54) BIOADHESIVE COMPOSITIONS AND METHODS FOR TOPICAL ADMINISTRATION OF ACTIVE AGENTS

(75) Inventors: Juan Mantelle, Miami; David Houze, Coconut Grove; David Kanios, Miami, all of FL (US)

(73) Assignee: Noven Pharmaceuticals, Inc., Miami, FL (US)

( * ) Notice: Subject to any disclaimer, the term of this patent is extended or adjusted under 35 U.S.C. 154(b) by 0 days.

(21) Appl. No.: 09/161,312

(22) Filed: Sep. 28, 1998

Related U.S. Application Data

(60) Provisional application No. 60/061,155, filed on Sep. 26, 1997.

(51) Int. Cl.$^7$ .......................... A61F 13/00; A61F 13/02; A61K 9/70; A61K 47/32; A61L 15/16
(52) U.S. Cl. ...................... 424/434; 424/443; 424/448; 514/772.5
(58) Field of Search .................. 424/435, 434, 424/443, 448, 2; 514/772.5

(56) References Cited

U.S. PATENT DOCUMENTS

| | | | | |
|---|---|---|---|---|
| 4,503,034 A | | 3/1985 | Maupetit et al. ............. 424/80 |
| 4,593,053 A | | 6/1986 | Jevne et al. ................ 523/111 |
| 4,740,365 A | * | 4/1988 | Yukimatsu et al. ......... 424/435 |
| 4,751,087 A | | 6/1988 | Wick ......................... 424/449 |
| 4,755,396 A | | 7/1988 | Geisler et al. ............. 427/197 |
| 4,764,378 A | | 8/1988 | Keith et al. ................. 424/435 |
| RE33,093 E | | 10/1989 | Schiraldi et al. ............ 424/676 |
| 4,889,720 A | | 12/1989 | Konishi ...................... 424/448 |
| 5,032,207 A | | 7/1991 | Sablotsky et al. ........... 156/250 |
| 5,047,244 A | * | 9/1991 | Sanvordeker et al. ....... 424/435 |
| 5,234,957 A | | 8/1993 | Mantelle ................... 514/772.6 |
| 5,346,701 A | * | 9/1994 | Heiber et al. ............... 424/435 |
| 5,446,070 A | | 8/1995 | Mantelle ................... 514/772.6 |
| 5,656,286 A | | 8/1997 | Miranda et al. |
| 6,210,699 B1 | | 4/2001 | Acharya et al. ............. 424/435 |

FOREIGN PATENT DOCUMENTS

| | | |
|---|---|---|
| DE | 2441626 | 3/1975 |
| DE | 2951319 | 7/1981 |
| EP | 507160 | 10/1992 |
| FR | 2 532 546 | 9/1982 |
| GB | 1050070 | 12/1966 |
| GB | 2 046 773 A | 11/1980 |
| JP | 63-160661 | 7/1988 |
| SE | 352 239 | 12/1972 |

* cited by examiner

Primary Examiner—Thurman K. Page
Assistant Examiner—Humera N. Sheikh
(74) Attorney, Agent, or Firm—Foley & Lardner

(57) ABSTRACT

Bioadhesive compositions in a flexible, finite form for topical application to skin or mucous membranes comprising a composition which results from an admixture of at least one PVP polymer, at least one bioadhesive, optionally a pharmaceutically acceptable solvent suitable for use with an active agent, and methods of administering active agents to a subject, are disclosed. The bioadhesive composition can either include an active agent incorporated directly in the composition, or a separate source of an active agent.

34 Claims, No Drawings

BIOADHESIVE COMPOSITIONS AND METHODS FOR TOPICAL ADMINISTRATION OF ACTIVE AGENTS

This application is based on provisional application 60/061,155 filed Sep. 26, 1997.

BACKGROUND OF THE INVENTION

1. Background of the Invention

This invention relates generally to bioadhesive compositions and methods for the topical administration of active agents to a mammal. More particularly, this invention relates to compositions capable of being used in wet or moist environments, especially on mucous membranes, for a prolonged period of time. There is no limitation on the type of drug that can be used in the present invention, provided that it can be topically administered. Thus, the active agent includes both drugs that are topically applied for local effects and those which can be administered topically for systemic effects.

2. Description of Related Art

Mucous membranes such as the mucosa of the buccal cavity have several physical attributes, such as a rich blood supply, that makes it a desirable site for topical administration of active agents for systemic delivery. Transmucosal delivery of active agents further avoids first-pass metabolism by the liver as well as poor uptake or inactivation via the gastrointestinal pathway. Examples of such agents include steroids such as estrogens, progestins and related compounds; androgens and anabolic steroids; non-steroidal anti-inflammatory agents such as ketoprofen; diclofenac; propranolol; thyroid hormones; pH sensitive peptides and small proteins such as insulin and ACTH; physostigmine; scopolamine; verapamil; and gallopamil.

Moreover, it is often desirable or necessary to deliver pharmaceutical agents locally, such as to alleviate pain in the buccal cavity.

Buccal and/or mucosal delivery compositions, devices and methods re disclosed, for example, in U.S. Pat. No. 3,972,995 to Tsuk, et al., U.S. Pat. No. 4,755,396 to Hsiao et al., U.S. Pat. No. 4,764,378 to Keith et al., U.S. Pat. No. 4,740,365 to Yukimatsu et al., U.S. Pat. No. 4,889,720 to Konishi et al U.S. Pat. No. 5,047,244 to Sanvordeker et al., and RE 33,093 to Schiraldi et al.

The use of bioadhesives in the administration of active agents to mucous membranes has been known for some time. The most commonly used bioadhesive compositions have "non-finite", (i.e., spreading substances which do not retain their form) and liquid or semi-liquid carriers such as pastes, gels, lotions, emulsions, creams, sprays, drops or ointments. Increasing use has been recently made of "finite" carriers (i.e., non-spreading substances which retain their form) such as films, dressings and bandages, or which start as finite then dissolve such as lozenges and tablets. Such compositions and devices have been less than satisfactory in achieving controlled release of such agents, and in maintaining adhesion (i.e., simply staying in place) or efficacy for prolonged periods of time. Moreover, they often leave unacceptable tacky residues upon removal.

It is disclosed in U.S. Pat. No. 5,446,070 to Mantelle, that concentrations of substantially dissolved anesthetic agents and other drugs as high as 50% by weight can be achieved in a system containing a bioadhesive carrier in which the adhesion of the carrier is not hindered. However, a need exists to increase the amount of time such compositions can be maintained at the site of administration in order to achieve maximum prolongation of therapeutic effects, both systemically and locally.

A successful bioadhesive device for topical administration of active agents for prolonged periods of time needs to satisfy a number of physical characteristics. For instance, the release liner should be easily peelable from the bioadhesive portion, yet the latter must be both sufficiently adhesive and cohesive to maintain close or intimate contact with the site of application for prolonged periods of time, typically between 1 to 2 hours, and up to even 24 hours with certain active agents. The bioadhesive composition must further retain the active agent at an appropriate rate for sustained or controlled delivery under the conditions prevailing in wet and moist environments associated with mucosa. In addition, the bioadhesive composition must be non-toxic, not cause chemical irritation and, must be easily removable with minimal mechanical irritation or damage to the application site.

In this regard, compositions according to the present invention are capable of adhering for prolonged periods of time, such as, for example, greater than 1 hour, preferably 2 hours, more preferably 4 hours, even more preferably greater than 8 hours, up to even 24 hours, to moist tissue such as mucosa and thus the desired therapeutic effects are ensured by the high degree of adhesion provided by the compositions of this invention.

SUMMARY OF THE INVENTION

This invention provides a bioadhesive composition comprising a mixture of at least two bioadhesive materials, especially comprising at least one soluble polyvinylpyrrolidone ("PVP") polymer, optionally in an admixture with a pharmaceutically acceptable solvent suitable for use with an active agent, the solvent optionally including a plasticizer for the bioadhesives. The bioadhesive compositions of this invention either include at least one active agent solubilized within the composition or, alternately, are used together with the topical administration of at least one active agent at the site of application, such as the means to adhere a drug reservoir to the application site.

In accordance with one aspect of the invention, an improved bioadhesive composition of a type which is suitable for prolonged adherence to wet or moist surfaces for controlled release of an active agent therefrom comprises a mixture of a polysaccharide, preferably a natural gum such as karaya gum, and a soluble PVP.

Optionally, the bioadhesive composition may further comprise a pressure-sensitive adhesive, preferably a solvent-based acrylic polymer.

In accordance with another aspect of the invention, the bioadhesive compositions provide for topical administration of two or more active agents of differing flux rates, in order to achieve prolonged and/or multiple therapeutic effects.

In accordance with yet another aspect of the invention, the bioadhesive composition also serves as a pressure-sensitive adhesive suitable for prolonged adherence to either wet/moist surfaces or dry surfaces, such as skin, for controlled release of an active agent therefrom.

This invention also relates to methods of administering the foregoing compositions.

In particular, the invention is directed to a bioadhesive composition in a flexible, finite form for topical application comprising:

(a) a mixture of two or more bioadhesives wherein at least one bioadhesive is a soluble PVP polymer;

(b) optionally a pharmaceutically acceptable solvent suitable for use with an active agent, the solvent optionally including a plasticizer for the bioadhesives;

(c) optionally, a pressure-sensitive adhesive;

wherein the composition is substantially free of water and substantially water insoluble; and wherein the composition either includes at least one active agent or, alternately, is used together with an active agent.

The invention further relates to a bioadhesive composition in a flexible, finite form for topical application comprising:

(a) a mixture of two or more bioadhesives wherein at least one bioadhesive is a soluble PVP polymer;

(b) optionally a pharmaceutically acceptable solvent suitable for use with an active agent, the solvent optionally including a plasticizer for the bioadhesives;

(c) in an admixture with at least two active agents, the at least two active agents comprising
   (i) combinations of the same active agent in free acid, free base and salt forms, or
   (ii) combinations of different active agents, each being delivered to a subject at a different flux rate;

(d) optionally, a pressure-sensitive adhesive; and wherein the composition is substantially free of water and substantially water insoluble.

The invention further relates to a composition in a flexible, finite form for topical application comprising:

(a) a mixture of two or more bioadhesives wherein at least one bioadhesive is a soluble PVP polymer;

(b) optionally a pharmaceutically acceptable solvent suitable for use with an active agent, the solvent optionally including a plasticizer for the bioadhesives;
   wherein the composition is substantially free of water, substantially water insoluble and is both a bioadhesive and a pressure-sensitive adhesive; and wherein the composition either includes at least one active agent or, alternately, is used together with an active agent.

The bioadhesive compositions further comprise a backing material and a release liner which conforms to the size and shape of an individual dosage unit or delivery system.

The invention also relates to a method of prolonged topical administration of one or more active agents to a subject comprising the steps of:

(a) providing a bioadhesive composition in a flexible, finite form comprising:
   (i) a mixture of two or more bioadhesives wherein at least one bioadhesive is a soluble PVP polymer;
   (ii) optionally a pharmaceutically acceptable solvent suitable for use with an active agent, the solvent optionally including a plasticizer for the bioadhesives;
   (iii) optionally, a pressure-sensitive adhesive;
   wherein the composition is substantially free of water and substantially water insoluble;

(b) contacting an area of skin or mucous membrane, preferably the oral mucosa, with said bioadhesive composition to administer the one or more active agents, wherein the composition either includes at least one active agent or, alternately, is used together with an active agent.

The invention additionally relates to a method of prolonged topical administration of two or more active agents to a subject comprising the steps of:

(a) providing a bioadhesive composition in a flexible, finite form comprising:
   (i) a mixture of two or more bioadhesives wherein at least one bioadhesive is a soluble PVP polymer;
   (ii) optionally a pharmaceutically acceptable solvent suitable for use with an active agent, the solvent optionally including a plasticizer for the bioadhesives;
   (iii) in an admixture with at least two active agents, the at least two active agents comprising
      (1) combinations of the same active agent in free acid, free base and salt forms, or
      (2) combinations of different active agents, each being delivered to a subject at a different flux rate;
   (iv) optionally, a pressure-sensitive adhesive;
   wherein the composition is substantially free of water and substantially water insoluble;

(b) contacting an area of skin or mucous membrane, preferably the oral mucosa, with said bioadhesive composition to administer the two or more active agents, wherein the composition either includes at least one active agent or, alternately, is used together with an active agent.

The present invention also includes a bioadhesive composition in a flexible, finite form for topical application of one or more active agents resulting from an admixture which comprises: (a) at least one soluble polyvinylpyrrolidone polymer (PVP); (b) at least one bioadhesive; (c) a therapeutically effective amount of one or more active agents; and (d) optionally one or more solvents.

The invention further includes a composition for administration of one or more active agents comprising: (a) a source of one or more active agents; and (b) an adhesive layer adapted for adhering to dermal or mucosal tissue and which results from an admixture which comprises: (i) at least one soluble polyvinylpyrrolidone polymer (PVP); (ii) at least one bioadhesive; and (iii) optionally one or more solvents, wherein the source (a) is different than the adhesive layer (b).

Further objects, features and advantages of the present invention will become apparent from consideration of the detailed description of preferred embodiments which follows.

DETAILED DESCRIPTION OF THE INVENTION INCLUDING PREFERRED EMBODIMENTS

This invention relates to bioadhesive compositions for the delivery of an active agent having local or systemic action, and methods of use thereof. The advantage of these bioadhesive compositions lies in their ability to maintain direct or intimate contact with the site of application for a prolonged periods of time, such as, for example, greater than 1 hour, preferably 2 hours, more preferably 4 hours, even more preferably greater than 8 hours, up to even 24 hours. It is believed the use of a soluble PVP polymer in combination with another bioadhesive, especially an insoluble bioadhesive, such as a natural gum, in a solvent that includes a plasticizer for the bioadhesives, allows each to swell (i.e., absorb moisture) independent of each other and consecutively rather than at the same time, such as when applied to mucosa, thus providing enhanced and prolonged adherence to wet or moist surfaces such as mucous membranes and teeth, and thereby increasing the effective penetration or absorption, and sustained delivery, of the active agent.

While not wishing to be bound by any theory, the inventors believe that the combination of PVP and another bioadhesive provides for a superior adhesion not attainable by either the PVP or other bioadhesive alone. It is believed that the presence of a bioadhesive, such as karaya gum, has the effect of preferentially absorbing and swelling with liquids, such as solvents, plasticizers and saliva which otherwise may interfere with the bioadhesive properties of the PVP. Thus, the addition of the other bioadhesive provides a faster acting and longer duration of adhesion.

The compositions are further provided in a finite, flexible form for convenient topical application of the active agent.

The present compositions do not substantially degrade during use and do not cause undue irritation or side effects which have been experienced with other transmucosal compositions of the prior art.

The term "bioadhesives" or "mucoadhesives" as used herein mean natural, synthetic or semi-synthetic materials that adhere and preferably strongly adhere to a surface such as skin, teeth or mucous membrane upon wetting or hydration. In order for a material to qualify as a bioadhesive, it must be capable of maintaining close or intimate contact with a wet or moist surface for a minimal amount of time.

The bioadhesive composition of the present invention is finite and "self adhesive" in that it is capable of attaching to the site of application without the need to reinforce such attachment by means of the use of another adhesive applied over it or to a backing.

A bioadhesive is frequently characterized as one that absorbs a certain number of times its weight in water (i.e., is water swellable). Depending on the bioadhesive, this can be as low as about 10 or as high as about 1000 times its weight it water. Exemplary bioadhesives are natural vegetable gums which absorb from about 30 to about 50 times their weight in water depending on the gum chosen.

Bioadhesion is often a difficult phenomenon to measure. The bioadhesive strength for purposes of this invention can be measured by standard tests for measuring force, e.g. in dynes per square centimeter, as disclosed in Robinson, U.S. Pat. No. 4,615,697, and is a minimum of 50 dynes per square centimeter, and more preferably 100 to 500 dynes per square centimeter or even 1,000 dynes per square centimeter.

The bioadhesive materials of the present invention include polymers, either water soluble or water insoluble, with or without crosslinking agents, known in the literature as being bioadhesive. There can be used for this purpose various bioadhesives including, preferably natural materials such as gums, carmelose, chitosan, carrageenans, eucheuma, fucoidan, hypnea, laminaran, furcellaran, agar, agarose, algin, amylose, scleroglucan, arabinoglactins, galactomannan, starches, alginates such as potassium and sodium, pectins, polypeptides such as gelatins, collagen and the like; cellulose materials including substituted and unsubstituted celluloses such as cellulose, ethycellalose, methylcellulose, nitrocellulose, propylcellulose, hydroxypropylcellulose, hydroxyethylcellulose, carboxymethylcellulose and hydroxypropylmethylcellulose, cellulose derivates, alkylcellulose and hydroxyalkylcellulose derivatives wherein the alkyl group is 1 to 7 carbons, cellulose acetate butyrate and carboxyalkylcellulose; synthetic and semi-synthetic polymers including carboxyvinyl copolymers, polyethylene glycol, polyethylene glycol ethers of aliphatic alcohols (such as cetyl, lauryl, oleyl and stearyl), polyhydroxyalkyl methacrylates, propylene glycol alginate, polyethylene oxides, polyacrylamides and polyacrylic acids; vinyl polymers such as polyvinyl alcohol, polyvinyl ethers, polyvinyl acetate and polyvinylpyrrolidones, and copolymerization and/or crosslinking of both hydrophilic and hydrophobic monomers such as hydroxyalkyl esters of acrylic and methacrylamide, and N-vinyl-2-pyrrolidone, alkyl acrylates and methacrylates, vinyl acetate, acrylonitrile and styrene; and generally, any physiologically acceptable polymer showing bioadhesive properties.

Particularly suitable bioadhesives include natural or synthetic polysaccharides. The term "polysaccharide" as used herein means a carbohydrate decomposable by hydrolysis into two or more molecules of monosaccharides or their derivatives. Suitable polysaccharides include cellulose materials, as specified above, pectin, a mixture of sulfated sucrose and aluminum hydroxide, N-vinyl lactam polysaccharides and most preferably natural gums such as karaya, guar, okra, arabic, acacia, pectina, ghatti, tragacanth, xanthan, locust bean, psyllium seed, tamarind, destria, casein and the like.

Some suitable polyacrylic acid polymers include polymers of acrylic acid crosslinked with polyalkenenyl ethers (generically known as carbomers) or divinyl glycol (generically known as polycarbophils) and commercially available from B. F. Goodrich, Cincinnati, Ohio, under the trademark Carbopole copolymers or resins, Pemulen polymeric emulsifiers and Noveon polycarbophils. Particularly preferred are Carbopol® 934 NF, 934P NF, 940 NF and 971P NF.

Exemprlary polyethylene glycol ethers of aliphatic alcohols include polyoxyethylene (4) lauryl ether, polyoxyethylene (2) oleyl ether and polyoxyethylene (10) oleyl ether which are sold under the trademark BRIJ® 30, 93 and 97 by ICI Americas, Inc., and BRIJ® 35, 52, 56, 58, 72, 76, 78, 92, 96, 700 and 721.

The term "polyvinylpyrrolidone" or "PVP" refers to a polymer, either a homopolymer or copolymer, containing vinylpyrrolidone (also referred to as N-vinylpyrrolidone, N-vinyl-2-pyrrolidone and N-vinyl-2-pyrrolidinone) as a monomeric unit. PVP polymers include soluble and insoluble homopolymeric PVPs, and copolymers such as vinylpyrrolidone/vinyl acetate and vinylpyrrolidone/dimethylamino-ethylmethacrylate. The cross-linked homopolymer is insoluble and is generally known in the pharmaceutical industry under the designations polyvinylpolypyrrolidone, crospovidone and PVP. The copolymer vinylpyrrolidone-vinyl acetate is generally known in the pharmaceutical industry under the designations Copolyvidon(e), Copolyvidonum or VP-VAc.

The term "soluble" when used with reference to PVP means that the polymer is soluble in water and generally is not substantially cross-linked, and has a molecular weight of less than about 2,000,000. See, generally, Buhler, KOLLIDON®: POLYVINYLPRYRROLIDONE FOR THE PHARMACEUTICAL INDUSTRY, BASF Aktiengesellschaft (1992). Soluble PVP polymers have been identified under in the pharmaceutical industry under a variety of names, the most commonly used include Povidone, Polyvidon(e), Polyvidonum, Polyvidonum, poly (N-vinyl-2-pyrrolidinone, poly (N-vinylbutyrolactam), poly (1-vinyl-2-pyrrolidone), poly [1-(2-oxo-1-pyrrolidinyl)ethylene].

The term "mucous membrane" or "mucosa" as used herein means oral, buccal, vaginal, rectal, nasal, intestinal and opthalmic surfaces.

The term "buccal" or "oral" as used herein means the mouth and the surrounding esophegeal area including the gums, teeth, palate, tongue, tonsils and periodontal tissue.

The term "adhesive" as used herein means a natural or synthetic material that is capable of sticking to the site of topical application or administration.

The term "topical" or "topically" is used herein in its conventional meaning as referring to direct contact with a spot on a mammal, which can be any anatomical site or surface area including skin, mucous membranes or hardened tissue such as bone, teeth or nails.

The term "administering" or "administration" is intended to mean any mode of application to a tissue which results in the physical contact of the composition with an anatomical site or surface area.

The term "subject" is intended to include all warm-blooded mammals, preferably humans.

As used herein, the term "prolonged" or "extended" refers to a time period of more than 30 minutes. The present composition is capable of being maintained in contact with mucosa, such as buccal mucosa, for a period of time up to 24 hours, preferably for periods ranging from about 30 minutes to about 24 hours, more preferably from about 1 hour to about 16 hours, and most preferably from about 1 hour to about 12 hours.

As used herein, the term "flux" is defined as the absorption of the active agent through the skin or mucosa, and is described by Fick's first law of diffusion:

$$J = -D(dC_m/dx),$$

where J is the flux in g/cm$^2$/sec, D is the diffusion coefficient of the drug through the skin or mucosa in cm2/sec and dCm/dx is the concentration gradient of the active agent across the skin or mucosa.

The phrase "flexible, finite form" is intended to mean a solid form capable of conforming to a surface with which it comes into contact, and which is capable of maintaining the contact in such solid form so as to facilitate topical application without any adverse physiological response, and without being appreciably decomposed by aqueous contact during administration to a subject.

An important characteristic of the embodiments of the present invention relates to the substantially water-free and water-insoluble nature of the composition. By the term "substantially water-free" is meant that the composition contains less than about 10% by weight water, and preferably less than 5%, and most preferably less than 3% prior to its topical application. In general, it is desirable to avoid the addition of water entirely and to eliminate, as far as possible, the presence of water in the other ingredients of the composition. By the term "substantially water-insoluble" is meant that the composition remains "finite" and does not generally detach from the site of application and under the conditions of regular, intended use for a period of at least 3 hours. The advantages to be derived from the substantially water-free and water-insoluble nature of the compositions of the present invention include achievement of higher concentrations of active agent. Another advantage of these compositions is minimization of precipitation of the active agent, which precipitation affects processing of the composition, affects rate of delivery of the active agents and in certain cases can affect sensitivity of the subject to the active agent.

The present compositions may in one embodiment include the use of two active agents which may be the same or different. For example, one agent may be in base form and the other agent may be in acid or salt form. In addition, one agent may be present which is delivered quickly having a relatively high flux rate, together with a second agent which is delivered over a prolonged time period and has a lower flux rate.

Specifically, the present composition permits the dosing of two or more active agents simultaneously. For example, a first agent could be present in the composition so as to be completely or substantially delivered after a period of, for example, about 1 to about 90 minutes, in particular for a period ranging from about 5 to about 60 minutes. At the same time, another active agent could be present in the composition such that the second agent is delivered over a longer time period, for example, up to a period of about 24 hours, in particular for a period ranging from about 5 minutes to about 16 hours. That is, in one embodiment of the present invention, the first agent would have an overall higher rate of flux than the second agent resulting in an earlier depletion of the first agent from the bioadhesive composition.

The period of time for delivering the active agents would depend on many factors, i.e., the dosing conditions, the agents being delivered, etc. For example, in accordance with the present invention, it would be possible to include a topical anesthetic agent which is delivered quickly, say within 20 minutes, and also include a second anesthetic agent which is the same or different from the first anesthetic and could optionally be systemic, which would be delivered over an extended period, say over a period of up to 8 hours or even 24 hours. Such an arrangement would be suitable for multiple applications, such as during dental procedures.

Alternatively, two or more active agents can be topically administered to achieve either a prolonged therapeutic effect or multiple therapeutic effects, or both. For example, a non-steroidal anti-inflammatory agent can be topically administered in conjunction with an anesthetic agent such that the bioadhesive composition provides a reduction in pain by means of both the analgesic effect and the anesthesia of the such agents, respectively. The intended effects of such a combination of agents, or other multiple combinations of agents, can be for a period of time up to 24 hours for the multiple agents, or for varying periods of time over a 24 hour period.

The rate of delivery of the active agents may be controlled by either the concentration and/or solubility of such agents in the bioadhesive composition, the pH of the composition, the thickness of the composition or the size of the system as a finished dosage form, or the permeability or solubility of the of the entire composition.

As used herein, the term "active agent" (and its equivalents, "agent," "bioactive agent," "drug," "medicament" and "pharmaceutical") is intended to have the broadest meaning and includes at least one of any therapeutic, prophylactic, pharmacological or physiological active substance, or mixture thereof, which is delivered to a mammal to produce a desired, usually beneficial, effect.

More specifically, any active agent which is capable of producing a pharmacological response, localized or systemic, irrespective of whether therapeutic, diagnostic or prophylactic in nature, is within the contemplation of the invention. It should be noted that the active agents or drugs may be used singularly or as a mixture of two or more agents or drugs, and in amounts sufficient to prevent, cure, diagnose, mitigate or treat a disease or condition, as the case may be.

1. α-Adrenergic agonists such as Adrafinil, Adrenolone, Amidephrine, Apraclonidine, Budralazine, Clonidine, Cyclopentamine, Detomidine, Dimetofrine, Dipivefrin, Ephedrine, Epinephrine, Fenoxazoline, Guanabenz, Guanfacine, Hydroxyamphetamine, Ibopamine, Indanazoline, Isometheptene, Mephentermine, Metaraminol, Methoxamine Hydrochloride, Methylhexaneamine, Metizolene, Midodrine, Naphazoline, Norepinephrine, Norfenefrine, Octodrine, Octopamine, Oxymetazoline, Phenylephrine Hydrochloride, Phenylpropanolamine Hydrochloride, Phenylpropylmethylamine, Pholedrine, Propylhexedrine, Pseudoephedrine, Rilmenidine, Synephrine, Tetrahydrozoline, Tiamenidine, Tramazoline, Tuaminoheptane, Tymazoline, Tyramine and Xylometazoline.

2. β-Adrenergic agonists such as Albuterol, Bambuterol, Bitolterol, Carbuterol, Clenbuterol, Clorprenaline, Denopamine, Dioxethedrine, Dopexamine, Ephedrine, Epinephrine, Etafedrine, Ethylnorepinephrine, Fenoterol, Formoterol, Hexoprenaline, Ibopamine, Isoetharine, Isoproterenal, Mabuterol, Metaproterenol, Methoxyphenamine, Oxyfedrine, Pirbuterol, Prenalterol, Procaterol, Protokylol, Reproterol, Rimiterol, Ritodrine, Soterenol, Terbuterol and Xamoterol.

3. α-Adrenergic blockers such as Amosulalol, Arotinolol, Dapiprazole, Doxazosin, Ergoloid Mesylates, Fenspiride, Indoramin, Labetalol, Nicergoline, Prazosin, Terazosin, Tolazoline, Trimazosin and Yohimbine.

4. β-Adrenergic blockers such as Acebutolol, Alprenolol, Amosulalol, Arotinolol, Atenolol, Befunolol, Betaxolol, Bevantolol, Bisoprolol, Bopindolol, Bucumolol, Befetolol, Bufuralol, Bunitrolol, Bupranolol, Butidrine Hydrochloride, Butofilolol, Carazolol, Carteolol, Carvedilol, Celiprolol, Cetamolol, Cloranolol, Dilevalol, Epanolol, Esmolol, Indenolol, Labetalol, Levobunolol, Mepindolol, Metipranalol, Metoprolol, Moprolol, Nadoxolol, Nifenalol, Nipradilol, Oxprenolol, Penbutolol, Pindolol, Practolol, Pronethalol, Propranolol, Sotalol, Sulfinalol, Talinolol, Tertatolol, Timolol, Toliprolol and Xibenolol.

5. Alcohol deterrents such as Calcium Cyanamide Citrated, Disulfiram, Nadide and Nitrefazole.

6. Aldose reductase inhibitors such as Epalrestat, Ponalrestat, Sorbinil and Tolrestat.

7. Anabolics such as Androisoxazole, Androstenediol, Bolandiol, Bolasterone, Clostebol, Ethylestrenol. Formyldienolone, 4-Hydroxy-19-nortestosterone, Methandriol, Methenolone, Methyltrienolone, Nandrolone, Nandrolone Decanoate, Nandrolone p-Hexyloxyphenylpropionate, Nandrolone Phenpropionate, Norbolethone, Oxymesterone, Pizotyline, Quinbolone, Stenbolone and Trenbolone.

8. Analgesics (dental) such as Chlorobutanol, Clove and Eugenol.

9. Analgesics (narcotic) such as Alfentanil, Allylprodine, Alphaprodine, Anileridine, Benzylmorphine, Bezitramide, Buprenorphine, Butorphanol, Clonitazene, Codeine, Codeine Methyl Bromide, Codeine Phosphate, Codeine Sulfate, Desomorphine, Dextromoramide, Dezocine, Diampromide, Dihydrocodeine, Dihydrocodeinone Enol Acetate, Dihydromorphine, Dimenoxadol, Dimepheptanol, Dimethylthiambutene, Dioxaphetyl Butyrate, Dipipanone, Eptazocine, Ethoheptazine, Ethylmethlythiambutene, Ethylmorphine, Etonitazene, Fentanyl, Hydrocodone, Hydrocodone Bitartrate, Hydromorphone, Hydroxypethidine, Isomethadone, Ketobemidone, Levorphanol, Lofentanil, Meperidine, Meptazinol, Metazocine, Methadone Hydrochloride, Metopon, Morphine, Morphine Derivatives, Myrophine, Nalbuphine, Narceine, Nicomorphine, Norlevorphanol, Normethadone, Normorphine, Norpipanone, Opium, Oxycodone, Oxymorphone, Papaveretum, Pentazocine, Phenadoxone, Phenazocine, Pheoperidine, Piminodine, Piritramide, Proheptazine, Promedol, Properidine, Propiram, Propoxyphene, Sufentanil and Tilidine.

10. Analgesics (non-narcotic) such as Acetaminophen, Acetaminosalol, Acetanilide, Acetylsalicylsalicylic Acid, Alclofenac, Alminoprofen, Aloxiprin, Aluminum Bis (acetylsalicylate),Aminochlorthenoxazin,2-Amino-4-picoline, Aminopropylon, Aminopyrine, Ammonium Salicylate, Antipyrine, Antipyrine Salicylate, Antrafenine, Apazone, Aspirin, Benorylate, Benoxaprofen, Benzpiperylon, Benzydamine, p-Bromoacetanilide, 5-Bromosalicylic Acid Acetate, Bucetin, Bufexamac, Bumadizon, Butacetin, Calcium Acetylsalicylate, Carbamazepine, Carbetidine, Carbiphene, Carsalam, Chloralantipyrine, Chlorthenoxazin(e), Choline Salicylate, Cinchophen, Ciramadol, Clometacin, Cropropamide, Crotethamide, Dexoxadrol, Difenamizole, Diflunisal, Dihydroxyaluminum Acetylsalicylate, Dipyrocetyl, Dipyrone, Emorfazone, Enfenamic Acid, Epirizole, Etersalate, Ethenzamide, Ethoxazene, Etodolac, Felbinac, Fenoprofen, Floctafenine, Flufenamic Acid, Fluoresone, Flupirtine, Fluproquazone, Flurbiprofen, Fosfosal, Gentisic Acid, Glafenine, Ibufenac, Imidazole Salicylate, Indomethacin, Indoprofen, Isofezolac, Isoladol, Isonixin, Ketoprofen, Ketorolac, p-Lactophenetide, Lefetamine, Loxoprofen, Lysine Acetylsalicylate, Magnesium Acetylsalicylate, Methotrimeprazine, Metofoline, Miroprofen, Morazone, Morpholine Salicylate, Naproxen, Nefopam, Nifenazone, 5' Nitro-2' propoxyacetanilide, Parsalmide, Perisoxal, Phenacetin, Phenazopyridine Hydrochloride, Phenocoll, Phenopyrazone, Phenyl Acetylsalicylate, Phenyl Salicylate, Phenyramidol, Pipebuzone, Piperylone, Prodilidine, Propacetamol, Propyphenazone, Proxazole, Quinine Salicylate, Ramifenazone, Rimazolium Metilsulfate, Salacetamide, Salicin, Salicylamide, Salicylamide O-Acetic Acid, Salicylsulfuric Acid, Salsalte, Salverine, Simetride, Sodium Salicylate, Sulfamipyrine, Suprofen, Talniflumate, Tenoxicam, Terofenamate, Tetradrine, Tinoridine, Tolfenamic Acid, Tolpronine, Tramadol, Viminol, Xenbucin and Zomepirac.

11. Androgens such as Androsterone, Boldenone, Dehydroepiandrosterone, Fluoxymesterone, Mestanolone, Mesterolone, Methandrostenolone, 17-Methyltestosterone, 17α-Methyltestosterone 3-Cyclopentyl Enol Ether, Norethandrolone, Normethandrone, Oxandrolone, Oxymesterone, Oxymetholone, Prasterone, Stanlolone, Stanozolol, Testosterone, Testosterone 17-Chloral Hemiacetal, Testosterone 17β-Cypionate, Testosterone Enanthate, Testosterone Nicotinate, Testosterone Pheynylacetate, Testosterone Propionate and Tiomesterone.

12. Anesthetics such as Acetamidoeugenol, Alfadolone Acetate, Alfaxalone, Amucaine, Amolanone, Amylocaine Hydrochloride, Benoxinate, Benzocaine, Betoxycaine, Biphenamine, Bupivacaine, Butacaine, Butaben, Butanilicaine, Burethamine, Buthalital Sodium, Butoxycaine, Carticaine, 2-Chloroprocaine Hydrochloride, Cocaethylene, Cocaine, Cyclomethycaine, Dibucaine Hydrochloride, Dimethisoquin, Dimethocaine, Diperadon Hydrochloride, Dyclonine, Ecgonidine, Ecgonine, Ethyl Aminobenzoate, Ethyl Chloride, Etidocaine, Etoxadrol, β-Eucaine, Euprocin, Fenalcomine, Fomocaine, Hexobarbital, Hexylcaine Hydrochloride, Hydroxydione Sodium, Hydroxyprocaine, Hydroxytetracaine, Isobutyl p-Aminobenzoate, Kentamine, Leucinocaine Mesylate, Levoxadrol, Lidocaine, Mepivacaine, Meprylcaine Hydrochloride, Metabutoxycaine Hydrochloride, Methohexital Sodium, Methyl Chloride, Midazolam, Myrtecaine, Naepaine, Octacaine, Orthocaine, Oxethazaine, Parethoxycaine, Phenacaine Hydrochloride, Phencyclidine, Phenol, Piperocaine, Piridocaine, Polidocanol, Pramoxine, Prilocaine, Procaine, Propanidid, Propanocaine, Proparacaine, Propipocaine, Propofol, Propoxycaine Hydrochloride, Pseudococaine, Pyrrocaine, Quinine Urea Hydochloride, Risocaine, Salicyl Alcohol, Tetracaine Hydrochloride, Thialbarbital, Thimylal, Thiobutabarbital, Thiopental Sodium, Tolycaine, Trimecaine and Zolamine.

13. Anorexics such as Aminorex, Amphecloral, Amphetamine, Benzaphetamine, Chlorphentermine, Clobenzorex, Cloforex, Clortermine, Cyclexedrine, Destroamphetamine Sulfate, Diethylpropion, Diphemethoxidine, N-Ethylamphetamine, Fenbutrazate, Fenfluramine, Fenproporex, Furfurylmethylamphetamine, Levophacetoperate, Mazindol, Mefenorex, Metamfeproamone, Methamphetamine, Norpseudoephedrine, Phendimetrazine, Phendimetrazine Tartrate, Phenmetrazine, Phenpentermine, Phenylpropanolamine Hydrochloride and Picilorex.

14. Anthelmintics (Cestodes) such as Arecoline, Aspidin, Aspidinol, Dichlorophen(e), Embelin, Kosin, Napthalene, Niclosamide, Pellertierine, Pellertierine Tannate and Quinacrine.

15. Anthelmintics (Nematodes) such as Alantolactone, Amoscanate, Ascaridole, Bephenium, Bitoscanate, Carbon Tetrachloride, Carvacrol, Cyclobendazole, Diethylcarbamazine, Diphenane, Dithiazanine Iodide, Dymanthine, Gentian Violet, 4-Hexylresorcinol, Kainic Acid, Mebendazole, 2-Napthol, Oxantel, Papain, Piperazine, Piperazine Adipate, Piperazine Citrate, Piperazine Edetate Calcium, Piperazine Tartrate, Pyrantel, Pyrvinium Pamoate, α-Santonin, Stilbazium Iodide, Tetrachloroethylene, Tetramisole, thiabendazole, Thymol, Thymyl N-Isoamylcarbamate, Triclofenol Piperazine and Urea Stibamine.

16. Anthelmintics (Onchocerca) such as Ivermectin and Suramin Sodium.

17. Anthelmintics (Schistosoma) such as Amoscanate, Amphotalide, Antimony Potassium Tartrate, Antimony Sodium Gluconate, Antimony Sodium Tartrate, Antimony Sodium Thioglycollate, Antimony Thioglycollamide, Becanthone, Hycanthone, Lucanthone Hydrochloride, Niridazole, Oxamniquine, Praziquantel, Stibocaptate, Stibophen and Urea Stibamine.

18. Anthelmintic (Trematodes) such as Anthiolimine and Tetrachloroethylene.

19. Antiacne drugs such as Adapelene, Algestone Acetophenide, Azelaic Acid, Benzoyl Peroxide, Cyoctol, Cyproterone, Motretinide, Resorcinol, Retinoic Acid, Tetroquinone and Tretinonine.

20. Antiallergics such as Amlexanox, Astemizole, Azelastine, Cromolyn, Fenpiprane, Histamine, Ibudilast, Nedocromil, Oxatomide, Pentigetide, Poison Ivy Extract, Poison Oak Extract, Poison Sumac Extract, Repirinast, Tranilast, Traxanox and Urushiol.

21. Antiamebics such as Arsthinol, Bialamicol, Carbarsone, Cephaeline, Chlorbetamide, Chloroquine, Chlorphenoxamide, Chlortetracycline, Dehydroemetine, Dibromopropamidine, Diloxanide, Dephetarsone, Emetine, Fumagillin, Glaucarubin, Glycobiarsol, 8-Hydroxy-7-iodo-5-quinolinesulfonic Acid, Iodochlorhydroxyquin, Iodoquinol, Paromomycin, Phanquinone, Phearsone Sulfoxylate, Polybenzarsol, Propamidine, Quinfamide, Secnidazole, Sulfarside, Teclozan, Tetracycline, Thiocarbamizine, Thiocarbarsone and Tinidazole.

22. Antiandrogens such as Bifluranol, Cyoctol, Cyproterone, Delmadinone Acetate, Flutimide, Nilutamide and Oxendolone.

23. Antianginals such as Acebutolol, Alprenolol, Amiodarone, Amlodipine, Arotinolol, Atenolol, Bepridil, Bevantolol, Bucumolol, Bufetolol, Bufuralol, Bunitrolol, Bupranolol, Carozolol, Carteolol, Carvedilol, Celiprolol, Cinepazet Maleate, Diltiazem, Epanolol, Felodipine, Gallopamil, Imolamine, Indenolol, Isosorbide Dinitrate, Isradipine, Limaprost, Mepindolol, Metoprolol, Molsidomine, Nadolol, Nicardipine, Nifedipine, Nifenalol, Nilvadipine, Nipradilol, Nisoldipine, Nitroglycerin, Oxprenolol, Oxyfedrine, Ozagrel, Penbutolol, Pentaerythritol Tetranitrate, Pindolol, Pronethalol, Propranolol, Sotalol, Terodiline, Timolol, Toliprolol and Verapamil.

24. Antiarrhythmics such as Acebutol, Acecaine, Adenosine, Ajmaline, Alprenolol, Amiodarone, Amoproxan, Aprindine, Arotinolol, Atenolol, Bevantolol, Bretylium Tosylate, Bubumolol, Bufetolol, Bunaftine, Bunitrolol, Bupranolol, Butidrine Hydrochloride, Butobendine, Capobenic Acid, Carazolol, Carteolol, Cifenline, Cloranolol, Disopyramide, Encainide, Esmolol, Flecainide, Gallopamil, Hydroquinidine, Indecainide, Indenolol, Ipratropium Bromide, Lidocaine, Lorajmine, Lorcainide, Meobentine, Metipranolol, Mexiletine, Moricizine, Nadoxolol, Nifenalol, Oxprenolol, Penbutolol, Pindolol, Pirmenol, Practolol, Prajmaline, Procainamide Hydrochloride, Pronethalol, Propafenone, Propranolol, Pyrinoline, Quinidine Sulfate, Quinidine, Sotalol, Talinolol, Timolol, Tocainide, Verapamil, Viquidil and Xibenolol.

25. Antiarteriosclerotics such as Pyridinol Carbamate.

26. Antiarthritic/Antirheumatics such as Allocupreide Sodium, Auranofin, Aurothioglucose, Aurothioglycanide, Azathioprine, Calcium 3-Aurothio-2-propanol-1-sulfonate, Celecoxib, Chloroquine, Clobuzarit, Cuproxoline, Diacerein, Glucosamine, Gold Sodium Thiomalate, Gold Sodium Thiosulfate, Hydroxychloroquine, Kebuzone, Lobenzarit, Melittin, Methotrexate, Myoral and Penicillamine.

27. Antibacterial (antibiotic) drugs including:
Aminoglycosides such as Amikacin, Apramycin, Arbekacin, Bambermycins, Butirosin, Dibekacin, Dihdrostreptomycin, Fortimicin(s), Gentamicin, Ispamicin, Kanamycin, Micronomicin, Neomycin, Neomycin Undecylenate, Netilmicin, Paromomycin, Ribostamycin, Sisomicin, Spectinomycin, Streptomycin, Streptonicozid and Tobramycin;
Amphenicols such as Azidamfenicol, Chloramphenicol, Chloramphenicol Palmitate, Chloramphenicol Pantothenate, Florfenicol and Thiamphenicol;
Ansamycins such as Rifamide, Rifampin, Rifamycin and Rifaximin;
β-Lactams, including:
  Carbapenems such as Imipenem;
  Cephalosporins such as Cefactor, Cefadroxil, Cefamandole, Cefatrizine, Cefazedone, Cefazolin, Cefixime, Cefmenoxime, Cefodizime, Cefonicid, Cefoperazone, Ceforanide, Cefotaxime, Cefotiam, Cefpimizole, Cefpirimide, Cefpodoxime Proxetil, Cefroxadine, Cefsulodin, Ceftazidime, Cefteram, Ceftezole, Ceftibuten, Ceftizoxime, Ceftriaxone, Cefuroxime, Cefuzonam, Cephacetrile Sodium, Cephalexin, Cephaloglycin, Cephaloridine, Cephalosporin, Cephalothin, Cephapirin Sodium, Cephradine and Pivcefalexin;
  Cephamycins such as Cefbuperazone, Cefmetazole, Cefminox, Cefetan and Cefoxitin;
  Monobactams such as Aztreonam, Carumonam and Tigemonam;
  Oxacephems such as Flomoxef and Moxolactam;
  Penicillins such as Amidinocillin, Amdinocillin Pivoxil, Amoxicillin, Ampicillan, Apalcillin, Aspoxicillin, Azidocillan, Azlocillan, Bacampicillin, Benzylpenicillinic Acid, Benzylpenicillin Sodium, Carbenicillin, Carfecillin Sodium, Carindacillin, Clometocillin, Cloxacillin, Cyclacillin, Dicloxacillin, Diphenicillin Sodium, Epicillin, Fenbenicillin, Floxicillin, Hetacillin, Lenampicillin, Metampicillin, Methicillin Sodium, Mezlocillin, Nafcillin Sodium, Oxacillin, Penamecillin, Penethamate Hydriodide, Penicillin G Benethamine, Penicillin G Benzathine, Penicillin G Benzhydrylamine, Penicillin G Calcium, Penicillin G Hydrabamine, Penicillin G Potassium, Penicillin G Procaine, Penicillen N, Penicillin O, Penicillin V, Penicillin V Benzathine, Penicillin V Hydrabamine, Penimepicycline, Phenethicillin Potassium, Piperacillin, Pivapicillin, Propicillin, Quinacillin, Sulbenicillin, Talampicillin, Temocillin and Ticarcillin;

Lincosamides such as Clindamycin and Lincomycin;

Macrolides such as Azithroimycin, Carbomycin, Clarithromycin, Erythromycin, Erythromycin Acistrate, Erythromycin Estolate, Erythromycin Glucoheptonate, Erythromycin Lactobionate, Erythromycin Propionate, Erythromycin Stearate, Josamycin, Leucomycins, Midecamycins, Miokamycin, Oleandomycin, Primycin, Rokitamycin, Rosaramicin, Roxithromycin, Spiramycin and Troleandomycin;

Polypeptides such as Amphomycin, Bacitracin, Capreomycin, Colistin, Enduracidin, Enviomycin, Fusafungine, Gramicidin(s), Gramicidin S, Mikamycin, Polymyxin, Polymyxin B-Methanesulfonic Acid, Pristinamycin, Ristocetin, Teicoplanin, Thiostrepton, Tuberactinomycin, Tyrocidine, Tyrothricin, Vancomycin, Viomycin, Viomycin Pantothenate, Virginiamycin and Zinc Bacitracin;

Tetracyclines such as Apicycline, Chlortetracycline, Clomocycline, Demeclocycline, Doxycycline, Guamecycline, Lymecycline, Meclocycline, Methacycline, Minocycline, Oxytetracycline, Penimepicycline, Pipacycline, Rolitetracycline, Sancycline, Senociclin and Tetracycline; and other antibiotics such as Cycloserine, Mupirocin and Tuberin.

28. Antibacterial drugs (synthetic), including:

2,4-Diaminopyrimidines such as Brodimoprim, Tetroxoprim and Trimethoprim;

Nitrofurans such as Furaltadone, Furazolium Chloride, Nifuradene, Nifuratel, Nifurfoline, Nifurpirinol, Nifurprazine, Nifurtoinol and Nitrofurantoin;

Quinolones and Analogs such as Amifloxacin, Cinoxacin, Ciprofloxacin, Difloxacin, Enoxacin, Fleroxacin, Flumequine, Lomefloxacin, Miloxacin, Nalidixic Acid, Norfloxacin, Ofloxacin, Oxolinic Acid, Pefloxacin, Pipemidic Acid, Piromidic Acid, Rosoxacin, Temafloxacin and Tosufloxacin;

Sulfonamides such as Acetyl Sulfamethoxypyrazine, Acetyl Sulfisoxazole, Azosulfamide, Benzylsulfamide, Chloramine-B, Chloramine-T, Dichloramine T, Formosulfathiazole, $N^2$Formylsulfisomidine, $N^2$-β-D-Glucosylsulfanilamide, Mafenide, 4'-(Methylsulfamoyl)sulfanilanilide, p-Nitrosulfathiazole, Noprylsulfamide, Phthalylsulfacetamide, Phthalylsulfathiazole, Salazosulfadimidine, Succinylsulfathiazole, Sulfabenzamide, Sulfacetamide, Sulfachlorpyridazine, Sulfachrysoidine, Sulfacytine, Sulfadiazine, Sulfadicramide, Sulfadimethoxine, Sulfadoxine, Sulfaethidole, Sulfaguanidine, Sulfaguanol, Sulfalene, Sulfaloxic Acid, Sulfamerazine, Sulfameter, Sulfamethazine, Sulfamethizole, Sulfamethomidine, Sulfamethoxazole, Sulfamethoxypyridazine, Sulfametrole, Sulfamidochrysoidine. Sulfamoxole, Sulfanilamide, Sulfanilamidomethanesulfonic Acid Triethanolamine Salt, 4-Sulfanilamidosalicylic Acid, N-Sulfanilylsulfanilamide, Sulfanilylurea, N-Sulfanilyl-3,4-xylamide, Sulfanitran, Sulfaperine, Sulfaphenazole. Sulfaproxyline, Sulfapyrazine, Sulfapyridine, Sulfasomizole, Sulfasymazine, Sulfathiazole, Sulfathiourea, Sulfatolamide, Sulfisomidine and Sulfisoxazole;

Sulfones such as Acedapsone, Acediasulfone, Acetosulfone Sodium, Dapsone, Diathymosulfone, Glucosulfone Sodium, Solasulfone, Succisulfone, Sulfanilic Acid, p-Sulfanilylbenzylamine, p,p'-Sulfonyldianiline-N.N'digalactoside, Sulfoxone Sodium and Thiazolsulfone; and others such as Clofoctol, Hexedine, Methenamine, Methenamine Anhydromethylene-citrate, Methenamine Hippurate, Methenamine Mandelate, Methenamine Sulfosalicylate, Nitroxoline and Xibornol.

29. Anticholinergics such as Adiphenine Hydrochloride, Alverine, Ambutonomium Bromide, Aminopentamide, Amixetrine, Amprotropine Phosphate, Anisotropine Methylbromide, Apoatropine, Atropine, Atropine N-Oxide, Benactyzine, Benapryzine, Benzetimide, Benzilonium Bromide, Benztropine Mesylate, Bevonium Methyl Sulfate, Biperiden, Butropium Bromide, N-Butylscopolammonium Bromide, Buzepide, Camylofine, Caramiphen Hydrochloride, Chlorbenzoxamine, Chlorphenoxamine, Cimetropium Bromide, Clidinium Bromide, Cyclodrine, Cyclonium Iodide, Cycrimine Hydrochloride, Deptropine, Dexetimide, Dibutoline Sulfate, Dicyclomine Hydrochloride, Diethazine, Difemerine, Dihexyverine, Diphemanil Methylsulfate, N-(1,2-Diphenylethyl) nicotinamide, Dipiproverine, Diponium Bromide, Emepronium Bromide, Endobenzyline Bromide, Ethopropazine, Ethybenztropine, Ethylbenzhydramine, Etomidoline, Eucatropine, Fenpiverinium Bromide, Fentonium Bromide, Flutropium Bromide, Glycopyrrolate, Heteronium Bromide, Hexocyclium Methyl Sulfate, Homatropine, Hyoscyamine, Ipratropium Bromide, Isopropamide, Levomepate, Mecloxamine, Mepenzolate Bromide, Metcaraphen, Methantheline Bromide, Methixene, Methscopolamine Bromide, Octamylamine, Oxybutynin Chloride, Oxyphencyclimine, Oxyphenonium Bromide, Pentapiperide, Penthienate Bromide, Phencarbamide, Phenglutarimide, Pipenzolate Bromide, Piperidolate, Piperilate, Poldine Methysulfate, Pridinol, Prifinium Bromide, Procyclidine, Propantheline Bromide, Propenzolate, Propyromazine, Scopolamine, Scopolamine N-Oxide, Stilonium Iodide, Stramonium, Sultroponium, Thihexinol, Thiphenamil, Tiemonium Iodide, Timepidium Bromide, Tiquizium Bromide, Tridihexethyl Iodide, Trihexyphenidyl Hydrochloride, Tropacine, Tropenzile, Tropicamide, Trospium Chloride, Valethamate Bromide and Xenytropium Bromide.

30. Anticonvulsants such as Acetylpheneturide, Albutoin, Aloxidone, Aminoglutethimide, 4-Amino-3-hydroxybutyric Acid, Atrolactamide, Beclamide, Buramate, Calcium Bromide, Carbamazepine, Cinromide, Clomethiazole, Clonazepam, Decimemide, Diethadione, Dimethadione, Doxenitoin, Eterobarb, Ethadione, Ethosuximide, Ethotoin, Fluoresone, Garbapentin, 5-Hydroxytryptophan, Lamotrigine, Lomactil, Magnesium Bromide, Magnesium Sulfate, Mephenytoin, Mephobarbital, Metharbital, Methetoin, Methsuximide, 5-Methyl-5-(3-phenanthryl) hydantoin, 3-Methyl-5-phenylhydantoin, Narcobarbital, Nimetazepam, Nitrazepam, Paramethadione, Phenacemide, Phenetharbital, Pheneturide, Phenobarbital, Phenobarbital Sodium, Phensuximide, Phenylmethylbarbituric Acid, Phenytoin, Phethenylate Sodium, Potassium Bromide, Pregabatin, Primidone, Progabide, Sodium Bromide, Sodium Valproate, Solanum, Strontium Bromide, Suclofenide, Sulthiame, Tetrantoin, Tiagabine, Trimethadione, Valproic Acid, Valpromide, Vigabatrin and Zonisamide.

31. Antidepressants, including:

Bicyclics such as Binedaline, Caroxazone, Citalopram, Dimethazan, Indalpine, Fencamine, Fluvoxamine Maleate, Indeloxazine Hydrochclride, Nefopam, Nomifensine, Oxitriptan, Oxypertine, Paroxetine, Sertraline, Thiazesim, Trazodone, Venlafaxine and Zometapine;

Hydrazides/Hydrazines such as Benmoxine, Iproclozide, Iproniazid, Isocarboxazid, Nialamide, Octamoxin and Phenelzine;

Pyrrolidones such as Cotinine, Rolicyprine and Rolipram;

Tetracyclics such as Maprotiline, Metralindole, Mianserin and Oxaprotiline.

Tricyclics such as Adinazolam, Amitriptyline, Amitriptylinoxide, Amoxapine, Butriptyline, Clomipramine, Demexiptiline, Desipramine, Dibenzepin, Dimetracrine, Dothiepin, Doxepin, Fluacizine, Imipramine, Imipramine N-Oxide, Iprindole, Lofepramine, Melitracen, Metapramine, Nortriptyline, Noxiptilin, Opipramol, Pizotyline, Propizepine, Protriptyline, Quinupramine, Tianeptine and Trimipramine; and others such as Adrafinil, Benactyzine. Bupropion, Butacetin, Deanol, Deanol Aceglumate, Deanol Acetamidobenzoate, Dioxadrol, Etoperidone, Febarbamate, Femoxetine, Fenpentadiol, Fluoxetine, Fluvoxamine, Hematoporphyrin, Hypercinin, Levophacetoperane, Medifoxamine, Minaprine, Moclobemide, Oxaflozane, Piberaline, Prolintane, Pyrisuccideanol, Rubidium Chloride, Sulpiride, Sultopride, Teniloxazine, Thozalinone, Tofenacin, Toloxatone, Tranylcypromine, L-Tryptophan, Viloxazine and Zimeldine.

32. Antidiabetics, including:

Biguanides such as Buformin, Metformin and Phenformin;

Hormones such as Glucagon, Insulin, Insulin Injection, Insulin Zinc Suspension, Isophane Insulin Suspension, Protamine Zinc Insulin Suspension and Zinc Insulin Crystals;

Sulfonylurea derivatives such as Acetohexamide, 1-Butyl-3-metanilylurea, Carbutamide, Chlorpropamide, Glibornuride, Gliclazide, Glipizide, Gliquidone, Glisoxepid, Glyburide, Glybuthiazol(e), Glybuzole, Glyhexamide, Glymidine, Glypinamide, Phenbutamide, Tolazamide, Tolbutamide and Tolcyclamide; and others such as Acarbose, Calcium Mesoxalate and Miglitol.

33. Antidiarrheal drugs such as Acetyltannic Acid, Albumin Tannate, Alkofanone, Aluminum Salicylates—Basic, Catechin, Difenoxin, Diphenoxylate, Lidamidine, Loperamide, Mebiquine, Trillium and Uzarin.

34. Antidiuretics such as Desmopressin, Felypressin, Lypressin, Ornipressin, Oxycinchophen, Pituitary—Posterior, Terlipressin and Vasopressin.

35. Antiestrogens such as Delmadinone Acetate, Ethamoxytriphetol, Tamoxifen and Toremifene.

36. Antifungal drugs (antibiotics), including:

Polyenes such as Amphotericin-B, Candicidin, Dermostatin, Filipin, Fungichromin, Hachimycin, Hamycin, Lucensomycin, Mepartricin, Natamycin, Nystatin, Pecilocin and Perimycin; and others such as Azaserine, Griseofulvin, Oligomycins, Neomycin Undecylenate, Pyrrolnitrin, Siccanin, Tubercidin and Viridin.

37. Antifungal drugs (synthetic), including:

Allylamines such as Naftifine and Terbinafine;

Imidazoles such as Bifonazole, Butoconazole, Chlordantoin, Chlormidazole, Cloconazole, Clotrimazole, Econazole, Enilconazole, Fenticonazole, Isoconazole, Ketoconazole, Miconazole, Omoconazole, Oxiconazole, Nitrate, Sulconazole and Tioconazole;

Triazoles such as Fluconazole, Itraconazole and Terconazole; and others such as Acrisorcin, Amorolfine, Biphenamine, Bromosalicylchloranilide, Buclosamide, Calcium Propionate, Chlophenesin, Ciclopirox, Cloxyquin, Coparaffinate, Diamthazole, Dihydrochloride, Exalamide, Flucytosine, Halethazole, Hexetidine, Loflucarban, Nifuratel, Potassium Iodide, Propionic Acid, Pyrithione, Salicylanilide, Sodium Propionate, Sulbentine, Tenonitrozole, Tolciclate, Tolindate, Tolnaftate, Tricetin, Ujothion, Undecylenic Acid and Zinc Propionate.

38. Antiglaucoma drugs such as Acetazolamide, Befunolol, Betaxolol, Bupranolol, Carteolol, Dapiprazoke, Dichlorphenamide, Dipivefrin, Epinephrine, Levobunolol, Methazolamide, Metipranolol, Pilocarpine, Pindolol and Timolol.

39. Antigonadotropins such as Danazol, Gestrinone and Paroxypropione.

40. Antigout drugs such as Allopurinol, Carprofen, Colchicine, Probenecid and Sulfinpyrazone.

41. Antihistamines, including:

Alkylamine derivatives such as Acrivastine, Bamipine, Bromphenir amine, Chlorpheniramine, Dimethindene, Metron S, Pheniramine, Pyrrobutamine, Thenaldine, Tolpropamine and Triprolidine;

Aminoalkyl ethers such as Bietanautine, Bromodiphenhydramine, Carbinoxamine, Clemastine, Diphenlypyraline, Doxylamine, Embrammine, Medrylamine, Mephenphydramine, p-Methyldiphenhydramine, Orphenadrine, Phenyltoloxamine, Piprinhydrinate and Setasine;

Ethylenediamine derivatives such as Alloclamide, p-Bromtripelennamine, Chloropyramine, Chlorothen, Histapyrrodine, Methafurylene, Methaphenilene, Methapyrilene, Phenbenzamine, Pyrilamine, Talastine, Thenyldiamine, Thonzylamine Hydrochloride, Tripelennamine and Zolamine;

Piperazines such as Cetirizine, Chlorcyclizine, Cinnarizine, Clocinizine and Hydroxyzine;

Tricyclics, including:

Phenothiazines such as Ahistan, Etymemazine, Fenethazine, N-Hydroxyethylpromethazine Chloride, Isopromethazine, Mequitazine, Promethazine, Pyrathiazine and Thiazinamium Methyl Sulfate; and others such as Azatadine, Clobenzepam, Cyroheptadine, Deptropine, Isothipendyl, Loratadine and Prothipendyl; and other antihistamines such as Antazoline, Astemizole, Azelastine, Cetoxime, Clemizole, Clobenztropine, Diphenazoline, Diphenhydramine, Fluticasone Propionate, Mebhydroline, Phenindamine, Terfenadine and Tritoqualine.

42. Antihyperlipoproteinemics, including:

Aryloxyalkanoic acid derivatives such as Beclorbrate, Bazafibrate, Binifibrate, Ciprofibrate, Clinofibrate, Clofibrate, Clofibric Acid, Etonfibrate, Fenofibrate, Gemfibrozil, Nicofibrate, Pirifibrate, Ronifibrate, Simfibrate and Theofibrate;

Bile acid sequesterants such as Cholestyramine Resin, Colestipol and Polidexide;

HMG CoA reductase inhibitors such as Fluvastatin, Lovastatin, Pravastatin Sodium and Simvastatin;

Nicotinic acid derivatives Aluminum Nicotinate, Acipimox, Niceritrol, Nicoclonate, Nicomol and Oxiniacic Acid;

Thyroid hormones and analogs such as Etiroxate, Thyropropic Acid and Thyroxine; and others such as Acifran, Azacosterol, Benfluorex, β-Benzalbutyramide, Carnitine, Chondroitin Sulfate, Clomestone, Detaxtran, Dextran Sulfate Sodium, 5,8, 11,14,17-Eicosapentaenoic Acid, Eritadenine, Furazbol, Meglutol, Melinamide, Mytatrienediol, Ornithine, γ-Oryzanol, Pantethine, Penataerythritol Tetraacetate, α-Phenylbutyramide, Pirozadil, Probucol, α-Sitosterol, Sultosilic Acid, Piperazine Salt, Tiadenol, Triparanol and Xenbucin.

43. Antihypertensive drugs, including:

Arylethanolamine derivatives such as Amosulalol, Bufuralol, Dilevalol, Labetalol, Pronethalol, Sotalol and Sulfinalol;

Aryloxypropanolamine derivatives such as Acebutolol, Alprenolol, Arotinolol, Atenolol, Betaxolol, Bevantolol, Bisoprolol, Bopindolol, Bunitrolol, Bupranolol, Butofilolol, Carazolol, Cartezolol, Carvedilol, Celiprolol, Cetamolol, Epanolol, Indenolol, Mepindolol, Metipranolol, Metoprolol, Moprolol, Nadolol, Nipradilol, Oxprenolol, Penbutolol, Pindolol, Propranolol, Talinolol, Tetraolol, Timolol and Toliprolol;

Benzothiadiazine derivatives such as Althiazide, Bendroflumethiazide, Benzthiazide, Benzylhydrochlorothiazide, Buthiazide, Chlorothiazide, Chlorthalidone, Cyclopenthiazide, Cyclothiazide, Diazoxide, Epithiazide, Ethiazide, Fenquizone, Hydrochlorothiazide, Hydroflumethiazide, Methyclothiazide, Meticrane, Metolazone, Paraflutizide, Polythiazide, Tetrachlormethiazide and Trichlormethiazide;

N-Carboxyalkyl (peptide/lactam) derivatives such as Alacepril, Captopril, Cilazapril, Delapril, Enalapril, Enalaprilat, Fosinopril, Lisinopril, Moveltipril, Perindopril, Quinapril and Ramipril;

Dihydropyridine derivatives such as Amlodipine, Felodipine, Isradipine, Nicardipine, Nifedipine, Nilvadipine, Nisoldipine and Nitrendipirne;

Guanidine derivatives such as Bethanidine, Debrisoquin, Guanabenz, Guanacline, Guanadrel, Guanazodine, Guanethidine, Guanfacine, Guanochlor, Guanoxabenz and Guanoxan;

Hydrazines and phthalazines such as Budralazine, Cadralazine, Dihydralazine, Endralazine, Hydracarbazine, Hydralazine, Pheniprazine, Pildralazine and Todralazine;

Imidazole derivatives such as Clonidine, Lofexidine, Phentolamine, Phentolamine Mesylate, Tiamenidine and Tolonidine;

Quaternary ammonium compounds Azamethonium Bromide, Chlorisondamine Chloride, Hexamethonium, Pentacynium Bis(methyl sulfate), Pentamethonium Bromide, Pentolinium Tartate, Phenactopinium Chloride and Trimethidiunum Methosulfate;

Quinazoline derivatives such as Alfuzosin, Bunazosin, Doxazosin, Prasosin, Terazosin and Trimazosin;

Reserpine derivatives such as Bietaserpine, Deserpidine, Rescinnamine, Reserpine and Syrosingopine;

Sulfonamide derivatives such as Ambuside, Clopamide, Furosemide, Indapamide, Quinethazone, Tripamide and Xipamide; and others such as Ajmaline, γ-Aminobutyric Acid, Bufeniode, Candesartan, Chlorthalidone, Cicletaine, Ciclosidomine, Cryptenamine Tannates, Eprosartan, Fenoldopam, Flosequinan, Indoramin, Irbesartan, Ketanserin, Losartan, Metbutamate, Mecamylamine, Methyldopa, Methyl 4-Pyridyl Ketone Thiosemicarbarzone, Metolazone, Minoxidil, Muzolimine, Pargyline, Pempidine, Pinacidil, Piperoxan, Primaperone, Protoveratrines, Raubasine, Rescimetol, Rilmenidene, Saralasin, Sodium Nitroprusside, Ticrynafen, Trimethaphan Camsylate, Tyrosinase, Urapidil and Valsartan.

44. Antihyperthyroids such as 2-Amino-4-methylthiazole, 2-Aminothiazole, Carbimazole, 3,5-Dibromo-L-tyrosine, 3,5-Diiodotyrosine, Hinderin, Iodine, Iothiouracil, Methimazole, Methylthiouracil, Propylthiouracil, Sodium Perchlorate, Thibenzazoline, Thiobarbital and 2-Thiouracil.

45. Antihypotensive drugs such as Amezinium Methyl Sulfate, Angiotensin Amide, Dimetofrine, Dopamine, Etifelmin, Etilefrin, Gepefrine, Metaraminol, Midodrine, Norepinephrine, Pholedrinead and Synephrine.

46. Antihypothyroid drugs such as Levothyroxine Sodium, Liothyronine, Thyroid, Thyroidin, Thyroxine, Tiatricol and TSH.

47. Anti-Inflammatory (non-steroidal) drugs, including:

Aminoarylcarboxylic acid derivatives such as Enfenamic Acid, Etofenamate, Flufenamic Acid, Isonixin, Meclofenamic Acid, Mefanamic Acid, Niflumic Acid, Talniflumate, Terofenamate and Tolfenamic Acid;

Arylacetic acid derivatives such as Acemetacin, Alclofenac, Amfenac, Bufexamac, Cinmetacin, Clopirac, Diclofenac Sodium, Etodolac, Felbinac, Fenclofenac, Fenclorac, Fenclozic Acid, Fentiazac, Glucametacin, Ibufenac, Indomethacin, Isofezolac, Isoxepac, Lonazolac, Metiazinic Acid, Oxametacine, Proglumetacin, Sulindac, Tiaramide, Tolmetin and Zomepirac;

Arylbutyric acid derivatives such as Bumadizon, Butibufen, Fenbufen and Xenbucin;

Arylcarboxylic acids such as Clidanac, Ketorolac and Tinoridine;

Arylpropionic acid derivatives such as Alminoprofen, Benoxaprofen, Bucloxic Acid, Carprofen, Fenoprofen, Flunoxaprofen, Flurbiprofen, Ibuprofen, Ibuproxam, Indoprofen, Ketoprofen, Loxoprofen, Miroprofen, Naproxen, Oxaprozin, Piketoprofen, Pirprofen, Pranoprofen, Protizinic Acid, Suprofen and Tiaprofenic Acid;

Pyrazoles such as Difenamizole and Epirizole;

Pyrazolones such as Apazone, Benzpiperylon, Feprazone, Mofebutazone, Morazone, Oxyphenbutazone, Phenybutazone, Pipebuzone, Propyphenazone, Ramifenazone, Suxibuzone and Thiazolinobutazone;

Salicylic acid derivatives such as Acetaminosalol, Aspirin, Benorylate, Bromosaligenin, Calcium Acetylsalicylate, Diflunisal, Etersalate, Fendosal, Gentisic Acid, Glycol Salicylate, Imidazole Salicylate, Lysine Acetylsalicylate, Mesalamine, Morpholine Salicylate, 1-Narhthyl Salicylate, Olsalazine, Parsalmide, Phenyl Acetylsalicylate, Phenyl Salicylate, Salacetamide, Salicylamine O-Acetic Acid, Salicylsulfuric Acid, Salsalate and Sulfasalazine;

Thiazinecarboxamides such as Droxicam, Isoxicam, Piroxicam and Tenoxicam; and others such as ε-Acetamidocaproic Acid, S-Adenosylmethionine, 3-Amino-4-hydroxybutyric Acid, Amixetrine, Bendazac, Benzydamine, Bucolome, Difenpiramide, Ditazol, Emorfazone, Guaiazulene, Nabumetone, Nimesulide, Orgotein, Oxaceprol, Paranyline, Perisoxal, Pifoxime, Proquazone, Proxazole and Tenidap.

48. Antimalarial drugs such as Acedapsone, Amodiaquin, Arteether, Artemether, Artemisinin, Artesunate, Bebeerine, Berberine, Chirata, Chlorguanide, Chloroquine, Chlorproguanil, Cinchona, Cinchonidine, Cinchonine, Cycloguanil, Gentiopicrin, Halofantrine, Hydroxychloroquine, Mefloquine Hydrochloride, 3-Methylarsacetin, Pamaquine, Plasmocid, Primaquine, Pyrimethamine, Quinacrine, Quinine, Quinine Bisulfate, Quinine Carbonate, Quinine Dihydrobromide, Quinine Dihydrochloride, Quinine Ethylcarbonate, Quinine Formate, Quinine Gluconate, Quinine Hydriodide, Quinine Hydrochloride, Quinine Salicylate, Quinine Sulfate, Quinine Tannate, Quinine Urea Hydrochloride, Quinocide, Quinoline and Sodium Arsenate Diabasic.

49. Antimigraine drugs such as Alpiropride, Dihydroergotamine, Eletriptan, Ergocornine, Ergocorninine, Ergocryptine, Ergot, Ergotamine, Flumedroxone acetate, Fonazine, Lisuride, Methysergid(e), Naratriptan, Oxetorone, Pizotyline, Rizatriptan and Sumatriptan.

50. Antinauseant drugs such as Acetylleucine Monoethanolamine, Alizapride, Benzquinamide, Bietanautine, Bromopride, Buclizine, Chlorpromazine, Clebopride, Cyclizine, Dimenhydrinate, Dipheniodol, Domperidone, Granisetron, Meclizine, Methalltal, Metoclopramide, Metopimazine, Nabilone, Ondansteron, Oxypendyl, Pipamazine, Piprinhydrinate, Prochlorperazine, Scopolamine, Tetrahydrocannabinols, Thiethylperazine, Thioproperzaine and Trimethobenzamide.

51. Antineoplastic drugs, including:

Alkylating agents, including:
Alkyl sulfonates such as Busulfan, Improsulfan and Piposulfan;
Aziridines such as Benzodepa, Carboquone, Meturedepa and Uredepa;
Ethylenimines and methylmelamines such as Altretamine, Triethylenemelamine, Triethylenephosphoramide, Triethylenethiophosphoramide and Trimethylolomelamine;
Nitrogen mustards such as Chlorambucil, Chlornaphazine, Chclophosphamide, Estramustine, Ifosfamide, Mechlorethamine, Mechlorethamine Oxide Hydrochloride, Melphalan, Novembichin, Phenesterine, Prednimustine, Trofosfamide and Uracil Mustard;
Nitrosoureas such as Carmustine, Chlorozotocin, Fotemustine, Lomustine, Nimustine and Ranimustine; and
others such as Camptothecin, Dacarbazine, Mannomustine, Mitobronitol, Mitolactol and Pipobroman;

Antibiotics such as Aclacinomycins, Actinomycin $F_1$, Anthramycin, Azaserine, Bleomycins, Cactinomycin, Carubicin, Carzinophilin, Chromomycins, Dactinomycin, Daunorubicin, 6-Diazo-5-oxo-L-norleucine, Doxorubicin, Epirubicin, Mitomycins, Mycophenolic Acid, Nogalamycin, Olivomycins, Peplomycin, Plicamycin, Porfiromycin, Puromycin, Streptonigrin, Streptozocin, Tubercidin, Ubenimex, Zinostatin and Zorubicin;

Antimetabolites, including:
Folic acid analogs such as Denopterin, Methotrexate, Pteropterin and Trimetrexate;
Purine analogs such as Fludarabine, 6-Mercaptopurine, Thiamiprine and Thioguanaine; and
Pyrimidine analogs such as Ancitabine, Azacitidine, 6-Azauridine, Carmofur, Cytarabine, Doxifluridine, Enocitabine, Floxuridine Fluroouracil and Tegafur;

Enzymes such as L-Asparaginase; and others such as Aceglatone, Amsacrine, Bestrabucil, Bisantrene, Bryostatin 1, Carboplatin, Cisplatin, Defofamide, Demecolcine, Diaziquone, Elfornithine, Elliptinium Acetate, Etoglucid, Etoposide, Gallium Nitrate, Hydroxyurea, Interferon-α, Interferon-β, Interferon-γ, Interleukine-2, Lentinan, Letrozole, Lonidamine, Mitoguazone, Mitoxantrone, Mopidamol, Nitracrine, Pentostatin, Phenamet, Pirarubicin, Podophyllinicc Acid, 2-Ethythydrazide, Polynitrocubanes, Procarbazine, PSK7, Razoxane, Sizofiran, Spirogermanium, Taxol, Teniposide, Tenuazonic Acid, Triaziquone, 2.2'.2"-Trichlorotriethylamine, Urethan, Vinblastine, Vincristine, Vindesine and Vinorelbine.

52. Antineoplastic (hormonal) drugs, including:

Androgens such as Calusterone, Dromostanolone Propionate, Epitiostanol, Mepitiostane and Testolactone;

Antiadrenals such as Aminoglutethimide, Mitotane and Trilostane;

Antiandrogens such as Flutamide and Nilutamide; and

Antiestrogens such as Tamoxifen and Toremifene.

53. Antineoplastic adjuncts including folic acid replenishers such as Frolinic Acid.

54. Antiparkinsonian drugs such as Amantadine, Benserazide, Bietanautine, Biperiden, Bromocriptine, Budipine, Cabergoline, Carbidopa, Deprenyl (a/k/a L-deprenyl, L-deprenil, L-deprenaline and selegiline), Dexetimide, Diethazine, Diphenhydramine, Droxidopa, Ethopropazine, Ethylbenzhydramine, Levodopa, Naxagolide, Pergolide, Piroheptine, Pramipexole, Pridinol, Prodipine, Quinpirole, Remacemide, Ropinirole, Terguride, Tigloidine and Trihexyphenidyl Hydrochloride.

55. Antipheochromocytoma drugs such as Metyrosine, Phenoxybenzamine and Phentolamine.

56. Antipneumocystis drugs such as Effornithine, Pentamidine and Sulfamethoxazole.

57. Antiprostatic hypertrophy drugs such as Gestonorone Caproate, Mepartricin, Oxendolone and Proscar7.

58. Antiprotozoal drugs (Leshmania) such as Antimony Sodium Gluconate, Ethylstibamine, Hydroxystilbamidine, N-Methylglucamine, Pentamidine, Stilbamidine and Urea Stibamine.

59. Antiprotozoal drugs (Trichomonas) such as Acetarsone, Aminitrozole, Anisomycin, Azanidazole, Forminitrazole, Furazolidone, Hachimycin, Lauroguadine, Mepartricin, Metronidazole, Nifuratel, Nifuroxime, Nimorazole, Secnidazole, Silver Picrate, Tenonitrozole and Tinidazole.

60. Antiprotozoal drugs (Trypanosma) such as Benznidazole, Eflornithine, Melarsoprol, Nifurtimox, Oxophenarsine, Hydrochloride, Pentamidine, Propamidine, Puromycin, Quinapyramine, Stilbamidine, Suramin Sodium, Trypan Red and Tryparasmide.

61. Antipuritics such as Camphor, Cyproheptadine, Dichlorisone, Glycine, Halometasone, 3-Hydroxycamphor, Menthol, Mesulphen, Methdilazine, Phenol, Polidocanol, Risocaine, Spirit of Camphor, Thenaldine, Tolpropamine and Trimeprazine.

62. Antipsoriatic drugs such as Acitretin, Ammonium Salicylate, Anthralin, 6-Azauridine, Bergapten(e), Chrysarobin, Etretinate and Pyrogallol.

63. Antipsychotic drugs, including:

Butyrophenones such as Benperidol, Bromperidol, Droperidol, Fluanisone, Haloperidol, Melperone, Moperone, Pipamperone, Sniperone, Timiperone and Trifluperidol;

Phenothiazines such as Acetophenazine, Butaperazine, Carphenazine, Chlorproethazine, Chlorpromazine, Clospirazine, Cyamemazine, Dixyrazine, Fluphenazine, Imiclopazine, Mepazine, Mesoridazine, Methoxypromazine, Metofenazate, Oxaflumazine, Perazine, Pericyazine, Perimethazine, Perphenazine, Piperacetazine, Pipotiazine, Prochlorperazine, Promazine, Sulforidazine, Thiopropazate, Thioridazine, Trifluoperazine and Triflupromazine;

Thioxanthenes such as Chlorprothixene, Clopenthixol, Flupentixol and Thiothixene;

other tricyclics such as Benzquinamide, Carpipramine, Clocapramine, Clomacran, Clothiapine, Clozapine, Opipramol, Prothipendyl, Tetrabenazine, and Zotepine; and others such as Alizapride, Amisulpride, Buramate, Fluspirilene, Molindone, Penfluridol, Pimozide, Spirilene and Sulpiride.

64. Antipyretics such as Acetaminophen, Acetaminosalol, Acetanilide, Aconine, Aconite, Aconitine, Alclofenac, Aluminum Bis(acetylsalicylate), Aminochlorthenoxazin, Aminopyrine, Aspirin, Benorylate, Benzydamine, Berberine, p-Bromoacetanilide, Bufexamac, Bumadizon, Calcium Acetysalicylate, Chlorthenoxazin(e), Choline Salicylate, Clidanac, Dihydroxyaluminum Acetylsalicylate, Dipyrocetyl, Dipyrone, Epirizole, Etersalate, Imidazole Salicylate, Indomethacin, Isofezolac, p-Lactophenetide, Lysine Acetylsalicylate, Magnesium Acetylsalicylate, Meclofenamic Acid, Morazone, Morpholine Salicylate, Naproxen, Nifenazone, 51-Nitro-2'-propoxyacetanilide, Phenacetin, Phenicarbazide, Phenocoll, Phenopyrazone, Phenyl Acetylsalicylate, Phenyl Salicylate, Pipebuzone, Propacetamol, Propyphenazone, Ramifenazone, Salacetamide, Salicylamide O-Acetic Acid, Sodium Salicylate, Sulfamipyrine, Tetrandrine and Tinoridine.

65. Antirickettsial drugs such as p-Aminobenzoic Acid, Chloramphenicol, Chloramphenicol Palmitate, Chloramphenicol Pantothenate and Tetracycline.

66. Antiseborrheic drugs such as Chloroxine, 3-O-Lauroylpyridoxol Diacetate, Piroctone, Pyrithione, Resorcinol, Selenium Sulfides and Tioxolone.

67. Antiseptics, including:

Guanidines such as Alexidine, Ambazone, Chlorhexidine and Picloxydine;

Halogens and halogen compounds such as Bismuth Iodide Oxide, Bismuth Iodosubgallate, Bismuth Tribromophenate, Bornyl Chloride, Calcium Iodate, Chlorinated Lime, Cloflucarban, Flurosalan, Iodic Acid, Iodine, Iodine Monochloride, Iodine Trichloride, Iodoform, Methenamine Tetraiodine, Oxychlorosene, Povidone-Iodine, Sodium Hypochlorite, Sodium Iodate, Symclosene, Thymol Iodide, Triclocarban, Triclosan and Troclosene Potassium;

Mercurial compounds such as Hydragaphen, Meralein Sodium, Merbromin, Mercuric Chloride, Mercuric Chloride, Ammoniated, Mercuric Sodium p-Phenolsulfonate, Mercuric Succinimide, Mercuric Sulfide, Red, Mercurophen, Mercurous Acetate, Mercurous Chloride, Mercurous Iodide, Nitromersol, Potassium Tetraiodomercurate(II), Potassium Triiodomercurate (II) Solution, Thimerfonate Sodium and Thimerosal;

Nitrofurans such as Furazolidone, 2-(Methoxymethyl)-5-nitrofuran, Nidroxyzone, Nifuroxime, Nifurzide and Nitrofurazone;

Phenols such as Acetomeroctol, Bithionol, Cadmium Salicylate, Carvacrol, Chloroxylenol, Clorophene, Cresote, Cresol(s), p-Cresol, Fenticlor, Hexachlorophene, 1-Napthyl Salicylate, 2-Napthyl Salicylate, 2,4,6-Tribromo-m-cresol, and 3',4',5'-Trichlorosalicylanilide;

Quinolines such as Aminoquinuride, Benzoxiquine, Broxyquinoline, Chloroxine, Chlorquinaldol, Cloxyquin, Ethylhydrocupreine, Euprocin, Halquinol, Hydrastine, 8-Hydroxquinoline, 8-Hydroxyquinoline Sulfate and Iodochlorhydroxyquin; and others such as Aluminum Acetate Solution, Aluminum Subacetate Solution, Aluminum Sulfate, 3-Amino-4-hydroxybutyric Acid, Boric Acid, Chlorhexidine, Chloroazodin, m-Cresyl Acetate, Cupric Sulfate, Dibromopropamidine, Ichthammol, Negatol7, Noxytiolin, Ornidazole, β-Propiolactone, α-Terpineol.

68. Antispasmodic drugs such as Alibendol, Ambucetamide, Aminopromazine, Apoatropine, Bevonium Methyl Sulfate, Bietamiverine, Butaverine, Butropium Bromide, N-Butylscopolammonium Bromide, Caroverine, Cimetropium Bromide, Cinnamedrine, Clebopride, Coniine Hydrobromide, Coniine Hydrochloride, Cyclonium Iodide, Difemerine, Diisopromine, Dioxaphetyl Butyrate, Diponium Bromide, Drofenine, Emepronium Bromide, Ethaverine, Feclemine, Fenalamide, Fenoverine, Fenpiprane, Fenpiverinium Brcmide, Fentonium Bromide, Flavoxate, Flopropione, Gluconic Acid, Guaiactamine, Hydramitrazine, Hymecromone, Leiopyrrole, Mebeverine, Moxaverine, Nafiverine, Octamylamine, Octaverine, Pentapiperide, Phenamacide Hydrochloride, Phloroglucinol, Pinaverium Bromide, Piperilate, Pipoxolan Hydrochloride, Pramiverin, Prifinium Bromide, Properidine, Propivane, Propyromazine, Prozapine, Racefemine, Rociverine, Spasmolytol, Stilonium Iodide, Sultroponium, Tiemonium Iodide, Tiquizium Bromide, Tiropramide, Trepibutone, Tricromyl, Trifolium, Trimebutine, N,N-lTrimethyl-3,3-diphenyl-propylamine, Tropenzile, Trospium Chloride and Xenytropium Bromide.

69. Antithrombotic drugs such as Anagrelide, Argatroban, Cilostazol, Chrysoptin, Daltroban, Defibrotide, Enoxaparin, Fraxiparine7, Indobufen, Lamoparan, Ozagrel, Picotamide, Plafibride, Reviparin, Tedelparin, Ticlopidine, Triflusal and Warfarin.

70. Antitussive drugs such as Allocamide, Amicibone, Benproperine, Benzonatate, Bibenzonium Bromide, Bromoform, Butamirate, Butethamate, Caramiphen Ethanedisulfonate, Carbetapentane, Chlophedianol, Clobutinol, Cloperastine, Codeine, Codeine Methyl Bromide, Codeine N-Oxide, Codeine Phosphate, Codeine Sulfate, Cyclexanone, Dextromethorphan, Dibunate Sodium, Dihydrocodeine, Dihydrocodeinone Enol Acetate, Dimemorfan, Dimethoxanate, α,α-Diphenyl-2-piperidinepropanol, Dropropizine, Drotebanol, Eprazinone, Ethyl Dibunate, Ethylmorphine, Fominoben, Guiaiapate, Hydrocodone, Isoaminile, Levopropoxyphene, Morclofone, Narceine, Normethadone, Noscapine, Oxeladin, Oxolamine, Pholcodine, Picoperine, Pipazethate, Piperidione, Prenoxdiazine Hydrochloride, Racemethorphan, Taziprinone Hydrochloride, Tipepidine and Zipeprol.

71. Antiulcerative drugs such as Aceglutamide Aluminum Complex, ε-Acetamidocaproic Acid Zinc Salt, Acetoxolone, Arbaprostil, Benexate Hydrochloride, Bismuth Subcitrate Sol (Dried), Carbenoxolone, Cetraxate, Cimetidine, Enprostil, Esaprazole, Famotidine, Ftaxilide, Gefarnate, Guaiazulene, Irsogladine, Misoprostol, Nizatidine, Omeprazole, Ornoprostil, γ-Oryzanol, Pifarnine, Pirenzepine, Plaunotol, Ranitidine, Rioprostil, Rosaprostol, Rotraxate, Roxatidine Acetate, Sofalcone, Spizofurone, Sucralfate, Teprenone, Trimoprostil, Thrithiozine, Troxipide and Zolimidine.

72. Antiurolithic drugs such as Acetohydroxamic Acid, Allopurinol, Potassium Citrate and Succinimide.

73. Antivenin drugs such as Lyovac7 Antivenin.

74. Antiviral drugs, including:
Purines and pyrimidinones such as Acyclovir, Cytarabine, Dideoxyadenosine, Dideoxycytidine, Dideoxyinosine, Edoxudine, Floxuridine, Ganciclovir, Idoxuridine, Inosine Pranobex, MADU, Penciclovir, Trifluridine, Vidrarbine and Zidovudiine; and
others such as Acetylleucine Monoethanolamine, Amantadine, Amidinomycin, Cosalane, Cuminaldehyde Thiosemicarbzone, Foscarnet Sodium, Imiquimod, Interferon-α, Interferon-β, Interferon-γ, Kethoxal, Lysozyme, Methisazone, Moroxydine, Podophyllotoxin, Ribavirin, Rimantadine, Stallimycin, Statolon, Tromantadine and Xenazoic Acid.

75. Anxiolytic drugs, including:
Arylpiperazines such as Buspirone, Gepirone, Ipsapirone and Tondospirone.
Benzodiazepine derivatives such as Alprazolam, Bromazepam, Camazepam, Chlordiazepoxide, Clobazam, Clorazepate, Chotiazepam, Cloxazolam, Diazepam, Ethyl Loflazepate, Etizolam, Fluidazepam, Flutazolam, Flutoprazepam, Halazepam, Ketazolam, Lorazepam, Loxapine, Medazepam, Metaclazepam, Mexazolam, Nordazepam, Oxazepam, Oxazolam, Pinazepam, Prazepam and Tofisopam;
Carbamates such as Cyclarbamate, Emylcamate, Hydroxyphenamate, Meprobamate, Phenprobamate and Tybamate; and
others such as Alpidem, Benzoctamine, Captodiamine, Chlormezanone, Etifoxine, Flesinoxan, Fluoresone, Glutamic Acid, Hydroxyzine, Lesopitron, Mecloralurea, Mephenoxalone, Mirtazepine, Oxanamide, Phenaglycodol, Suriclone and Zatosetron.

76. Benzodiazepine antagonists such as Flumazenil.

77. Bronchodilators, including:
Ephedrine derivatives such as Albuterol, Bambuterol, Bitolterol, Carbuterol, Clenbuterol, Clorprenaline, Dioxethedrine, Ephedrine, Epiniphrine, Eprozinol, Etafedrine, Ethylnorepinephrine, Fenoterol, Hexoprenaline, Isoetharine, Isoproterenol, Mabuterol, Metaproterenol, N-Methylephedrine, Pirbuterol, Procaterol, Protokylol, Reproterol, Rimiterol, Salmeterol, Soterenol, Terbutaline and Tulobuterol;
Quaternary ammonium compounds such as Bevonium Methyl Sulfate, Clutropium Bromide, Ipratropium Bromide and Oxitropium Bromide;
Xanthine derivatives such as Acefylline, Acefylline Piperazine, Ambuphylline, Aminophylline, Bamifylline, choline Theophyllinate, Doxofylline, Dyphylline, Enprofylline, Etamiphyllin, Etofylline, Guaithylline, Proxyphylline, Theobromine, 1-Theobromineacetic Acid and Theophylline; and
others such as Fenspiride, Medibazine, Montekulast, Methoxyphenanime, Tretoquinol and Zafirkulast.

78. Calcium channel blockers, including:
Arylalkylamines such as Bepridil, Ditiazem, Fendiline, Gallopanil, Prenylamine, Terodiline and Verapamil;
Dihydropyridine derivatives such as Felodipine, Isradipine, Nicardipine, Nifedipine, Nilvadipine, Nimodipine, Nisoldipine and Nitrendipine;
Piperazine derivatives such as Cinnarizine, Flunarisine and Lidoflazine; and
others such as Bencyclane, Etafenone and Perhexiline.

79. Calcium regulators such as Calcifediol, Calcitonin, Calcitriol, Clodronic Acid, Dihydrotachysterol, Elcatonin, Etidronic Acid, Ipriflavone, Pamidronic Acid, Parathyroid Hormone and Teriparatide Acetate.

80. Cardiotonics such as Acefylline, Acetyldigititoxins, 2-Amino-4-picoline, Amrinone, Benfurodil Hemisuccinate, Buclasdesine, Cerberoside, Camphotamide, Convallatoxin, Cymarin, Denopamine, Deslanoside, Ditalin, Digitalis, Digitoxin, Digoxin, Dobutamine, Dopamine, Dopexamine, Enoximone, Erythrophleine, Fenalcomine, Gitalin, Gitoxin, Glycocyamine, Heptaminol, Hydrastinine, Ibopamine, Lanotodises, Metamivam, Milrinone, Neriifolin, Oleandrin, Ouabain, Oxyfedrine, Prenalterol, Proscillaridin, Resibufogenin, Scillaren, Scillarenin, Strophanthin, Sulmazole, Theobromine and Xamoterol.

81. Chelating agents such as Deferozmine, Ditiocarb Sodium, Edetate Calcium Disodium, Edetate Disodium, Edeate Sodium, Edetate Trisodium, Penicillamine, Pentetate Calcium Trisodium, Pentectic Acid, Succimer and Trientine;

82. Cholecystokinin antagonists such as Proglumide.

83. Cholelitholytic agents such as Chenodiol, Methyl tert-Butyl Ether, Monooctanoin and Ursodiol.

84. Choleretics such as Alibendol, Anethole Trithion, Azintamide, Cholic Acid, Cicrotoic Acid, Clanobutin, Cyclobutyrol, Cyclovalone, Cynarin(e), Dehydrocholic Acid, Deoxycholic Acid, Dimecrotic Acid, α-Ethylbenzyl Alcohol, Exiproben, Feguprol, Fencibutirol, Fenipentol, Florantyrone, Hymecromone, Menbutone, 3-(o-Methoxyphenyl)-2-phenylacrylic Acid, Metochalcone, Moquizone, Osalmid, Ox Bile Extract, 4.4'-Oxydi-2-butanol, Piprozolin, Prozapine, 4-Salicyloylmorpholine, Sincalide, Taurocholic Acid, Timonacic, Tocamphyl, Trepibutone and Vanitiolide.

85. Cholinergic agents such as Aceclidine, Acetylcholide Bromide, Acetylcholide Chloride, Aclatonium Napadisilate, Benzpyrinium Bromide, Bethanechol chloride, Carbachol, Carpronium chloride, Demecarium Bromide, Dexpanthenol, Diisopropyl Paraoxon, Echothiophate Iodide, Edrophomium chloride, Eseridine, Furtrethonium, Isoflurophate, Methacholine chloride, Muscarine, Neostigmine, Oxapropanium Iodide, Physostigmine and Pyridostigmine Bromide.

86. Cholinesterase inhibitors such as Ambenonium Chloride, Distigmine Bromide and Galanthamine.

87. Cholinesterase reactivators such as Obidoximine Chloride and Pralidoxime Chloride.

88. Central nervous system stimulants and agents such as Amineptine, Amphetimine, Amphetaminil, Bemegride, Benzphetamine, Brucine, Caffeine, Chlorphentermine, Clofenciclan, Clortermine, Coca, Demanyl Phosphate, Dexoxadrol, Dextroamphetamine Sulfate, Diethlpropion, N-Ethylamphetamine, Ethamivan, Etifelmin, Etryptamine, Fencamfamine, Fenethylline, Fenosolone, Flurothyl, Galanthamine, Hexacyclonate Sodium, Homocamfin, Mazindol, Megexamide, Methamphetamine, Methylphenidate, Nikethamide, Pemoline, Pentylenetetrazole, Phenidimetrazine, Phenmetrazine, Phentermine, Picrotoxin, Pipradrol, Prolintane and Pyrovalerone.

89. Decongestants such as Amidephrine, Cafaminol, Cyclopentamine, Ephedrine, Epinephrine, Fenoxazoline, Indanazoline, Metizoline, Naphazoline, Nordefrine Hydrochloride, Octodrine, oxymetazoline, Phenylephrine Hydrochloride, Phenylpropanolamine Hydrochloride, Phenylpropylmethylamine, Propylhexedrine, Pseudoephedrine, Tetrahydrozoline, Tymazoline and Xylometazoline.

90. Dental agents, including:

Bisphosphonates (anti-periodontal disease and bone resorption) such as Alendronate, Clodronate, Etidronate, Pamidronate and Tiludronate; Carries Prophylactics such as Arginine and Sodium Fluoride; Desensitizing Agents such as Potassium Nitrate and Citrate Oxalate.

91. Depigmentors such as Hydroquinine, Hydroquinone and Monobenzone.

92. Diuretics, including:

Organomercurials such as Chlormerodrin, Meralluride, Mercamphamide, Mercaptomerin Sodium, Mercumallylic Acid, Mercumatilin Sodium, Mercurous Chloride and Mersalyl;

Pteridines such as Furterene and Triamterene;

Purines such as Acefylline, 7-Morpholinomethyltheophylline, Pamabrom, Protheobromine and Theobromine;

Steroids such as Canrenone, Oleandrin and Spironolactone;

Sulfonamide derivatives such as Acetazolmide, Ambuside, Azosemide, Bumetanide, Butazolamide, Chloraminophenamide, Clofenamide, Clopamide, Clorexolene, Diphenylmethane-4.4'-disulfonamide, Disulfamide, Ethbxzolamide, Furosemide, Indapamide, Mefruside, Methazolamide, Piretanide, Quinethazone, Torasemide, Tripamide and Xipamide;

Uracils such as Aminometradine and Amisometradine;

others such as Amanozine, Amiloride, Arbutin, Chlorazanil, Ethacrynic Acid, Etozolin, Hydracarbazine, Isosorbide, Mannitol, Metochalcone, Muzolimine, Perhexiline, Ticrynafen and Urea.

93. Dopamine receptor agonists such as Bromocriptine, Dopexamine, Fenoldopam, Ibopamine, Lisuride, Naxagolide and Pergolide.

94. Ectoparasiticides such as Amitraz, Benzyl Benzoate, Carbaryl, Crotamiton, DDT, Dixanthogen, Isobornyl Thiocyanoacetate—Technical, Lime Sulfurated Solution, LIndane, Malathion, Mercuric Oleate, Mesulphen and Sulphur—Pharmaceutical.

95. Enzymes, including:

Digestive enzymes such as α-Amylase (Swine Pancreas), Lipase, Pancrelipase, Pepsin and Rennin;

Mucolytic enzymes such as Lysozyme;

Penicillin inactivating enzymes such as Penicillinase; and

Proteolytic enzymes such as Collagenase, Chymopapain, Chymotrypsins, Papain and Trypsin.

96. Enzyme inducers (hepatic) such as Flumecinol.

97. Estrogens, including:

Nonsteroidal estrogens such as Benzestrol, Broparoestrol, Chlorotrianisene, Dienestrol, Diethylstilbestrol, Diethylstilbestrol Diproprionate, Dimestrol, Fosfestrol, Hexestrol, Methallenestril and Methestrol; and Steroidal estrogens such as Colpormon, Conjugated Estrogenic Hormones, Equilenin, Equilin, Estradiol, Estradiol Benzoate, Estradiol 17β-Cypionate, Estriol, Estrone, Ethinyl Estradiol, Mestranol, Moxestrol, Mytatrienediol, Quinestradiol and Quinestrol.

98. Gastric secretion inhibitors such as Enterogastrone and Octreotide.

99. Glucocorticoids such as 21-Acetoxyprefnenolone, Aalclometasone, Algestone, Amicinonide, Beclomethasone, Betamethasone, Budesonide, Chloroprednisone, Clobetasol, Blovetasone, Clocortolone, Cloprednol, Corticosterone, Cortisone, Cortivazol, Deflazacort, Desonide, Desoximetasone, Dexamethasone, Diflorasone, Diflucortolone, Difluprednate, Enoxolone, Fluazacort, Flucloronide, Flumehtasone, Flunisolide, Fluocinolone Acetonide, Fluocinonide, Fluocortin Butyl, Fluocortolone, Fluorometholone, Fluperolone Acetate, Fluprednidene Acetate, Fluprednisolone, Flurandrenolide, Formocortal, Halcinonide, Halometasone, Halopredone Acetate, Hydrocortamate, Hydrocortisone, Hydrocortisone Acetate, ydrocortisone Phosphate, Hydrocortisone 21-Sodium Succinate, Hydrocortisone Tebutate, Mazipredone, Medrysone, Meprednisone, Methyolprednisolone, Mometasone Furoate, Paramethasone, Prednicarbate, Prednisolone, Prednisolone 21-Diethylaminoacetate, Prednisone Sodium Phosphate, Prednisolone Sodium Succinate, Prednisolone Sodium 21-m-Sulfobenzoate, Prednisolone 21-Stearoylglycolate, Prednisolone Tebutate, Prednisolone 21-Trimethylacetate, Prednisone, Prednival, Prednylidene, Prednylidene 21-Diethylaminoacetate, Tixocortal, Triamcinolone, Triamcinolone Acetonide, Triamcinolone Benetonide and Triamcinolone Hexacetonide.

100. Gonad-Stimulating principles such as Buserelin, Clomiphene, Cyclofenil, Epimestrol, FSH, HCG and LH-RH.

101. Gonadotropic hormones such as LH and PMSG.

102. Growth hormone inhibitors such as Octreotide and Somatostatin.

103. Growth hormone releasing factors such as Semorelin.

104. Growth stimulants such as Somatotropin.

105. Hemolytic agents such as Phenylhydrazine and Phenylhydrazine Hydrochloride.

106. Heparin antagonists such as Hexadimethrine Bromide and Protamines.

107. Hepatoprotectants such as S-Adenosylmethionine, Betaine, Catechin, Citolone, Malotilate, Orazamide, Phosphorylcholine, Protoporphyrin IX, Silymarin-Group, Thiotic Acid and Tiopronin.

108. Immunomodulators such as Amiprilose, Bucillamine, Ditiocarb Sodium, Inosine Pranobex, Interferon-γ, Interleukin-2, Lentinan, Muroctasin, Platonin, Procodazole, Tetramisole, Thymomodulin, Thymopentin and Ubenimex.

109. Immunosuppressants such as Azathioprine, Cyclosporins and Mizoribine.

110. Ion exchange resins such as Carbacrylic Resins, Cholestyramine Resin, Colestipol, Polidexide, Resodec and Sodium Polystyrene Sulfonate.

111. Lactation stimulating hormone such as Prolactin.

112. LH-RH agonists such as Buserelin, Goserelin, Leuprolide, Nafarelin, and Triptorelin.

113. Lipotropic agents such as N-Acetylmethionine, Choline Chloride, Choline Dehydrocholate, Choline Dihydrogen Citrate, Inositol, Lecithin and Methionine.

114. Lupus erythematosus suppressants such as Bismuth Sodium Triglycollamate, Bismuth Subsalicylate, Chloroquine and Hydroxychloroquine.

115. Mineralcorticoids such as Aldosterone, Deoxycorticosterone, Deoxycorticosterone Acetate and Fludrocortisone.

116. Miotic drugs such as Carbachol, Physostigmine, Pilocarpine and Pilocarpus.

117. Monoamine oxidase inhibitors such as Deprenyl, Iproclozide, Iproniazid, Isocarboxazid, Moclobemide, Octomoxin, Pargyline, Phenelzine, Phenoxypropazine, Pivalylbenzhydrazine, Prodipine, Toloxatone and Tranylcypromine.

118. Mucolytic agents such as Acetylcysteine, Bromhexine, Carbocysteine, Domiodol, Letosteine, Lysozyme, Mecysteine Hydrochloride, Mesna, Sobrerol, Stepronin, Tiopronin and Tyloxapol.

119. Muscle relaxants (skeletal) such as Afloqualone, Alcuronium, Atracurium Besylate, Baclofen, Benzoctamine, Benzoquinonium Chloride, C-Calebassine, Carisoprodol, Chlormezanone, Chlorphenesin Carbamate, Chlorproethazine, Chlozoxazone, Curare, Cyclarbamate, Cyclobenzaprine, Dantrolene, Decamethonium Bromide, Diazepam, Eperisone, Fazadinium Bromide, Flumetramide, Gallamine Triethiodide, Hexacarbacholine Bromide, Hexafluorenium Bromide, Idrocilamide, Laueximum Methyl Sulfate, Leptodactyline, Memantine, Mephenesin, Mephenoxalone, Metaxalone, Methocarbamol, Metocurine Iodide, Nimetazepam, Orphenadrine, Pancuronium Bromide, Phenprobamate, Phenyramidol, Pipecurium Bromide, Promoxolane, Quinine Sulfate, Styramate, Succinylcholine Bromide, Succinylcholine Chloride, Succinylcholine Iodine, Suxethonium Bromide, Tetrazepam, Thiocolchicoside, Tizanidine, Tolperisone, Tubocurarine Chloride, Vecuronium Bromide and Zoxolamine.

120. Narcotic antagonists such as Amiphenazole, Cyclazocine, Levallorphan, Nadide, Nalmfene, Nalorphine, Nalorphine Dinicotinate, Naloxone and Naltrexone.

121. Neuroprotective agents such as Dizocilpine.

122. Nootropic agents such as Aceglutamide, Acetylcarnitine, Aniracetam, Bifematlane, Exifone, Fipexide, Idebenone, Indeloxazune Hydrochloride, Nizofenone, Oxiracetam, Piracetam, Propentofylline, Pyritinol and Tacrine.

123. Ophthalmic agents such as 15-ketoprostaglandins.

124. Ovarian hormone such as Relaxin.

125. Oxytocic drugs such as Carboprost, Cargutocin, Deaminooxytocin, Ergonovine, Gemeprost, Methylergonovine, Oxytocin, Pituitary (Posterior), Prostaglandin $E_2$, Prostaglandin $F_{2a}$ and Sparteine.

126. Pepsin inhibitors such as Sodium Amylosulfate.

127. Peristaltic stimulants such as Cisapride.

128. Progestogens such as Allylestrenol, Anagestone, Chlormadinone Acetate, Delmadinone Acetate, Demegestone, Desogestrel, Dimethisterone, Dydrogesterone, Ethisterone, Ethynodiol, Flurogestone Acetate, Gestodene, Gestonorone Caproate, Haloprogesterone, 17-Hydroxy-16-methylene—progesterone, 17α-Hydroxyprogesterone, 17α-Hydroxygesterone Caproate, Lynestrenol, Medrogestone, Medroxyprogesterone, Megestrol Acetate, Melengestrol, Norethindrone, Norethynodrel, Norgesterone, Norgestimate, Norgestrel, Norgestrienone, Norvinisterone, Pentagestrone, Progesterone, Promegestone, Quingestrone and Trengestone.

129. Prolactin inhibitors such as Metergoline.

130. Prostaglandins and prostaglandin analogs such as Arbaprostil, Carboprost, Enprostil, Bemeprost, Limaprost, Misoprostol, Ornoprostil, Prostacyclin, Prostaglandin $E_1$, Prostaglandin $E_2$, Prostagland in $F_{2a}$, Rioprostil, Rosaprostol, Sulprostone and Trimoprostil.

131. Protease inhibitors such as Aprotinin, Camostat, Gabexate and Nafamostat.

132. Respiratory stimulants such as Almitrine, Bemegride, Carbon Dioxide, Cropropamide, Crotethamide, Dimefline, Dimorpholamine, Doxapram, Ethamivan, Fominoben, Lobeline, Mepixanox, Metamivam, Nikethamide, Picrotoxin, Pimeclone, Pyridofylline, Sodium Succinate and Tacrine.

133. Sclerosing agents such as Ethanolamine, Ethylamine, 2-Hexyldecanoic Acid, Polidocanol, Quinine Bisulfate, Quinine Urea Hydrochloride, Sodium Ricinoleate, Sodium Tetradecyl Sulfate and Tribenoside.

134. Sedatives and hypnotics, including:

Acyclic ureides such as Acecarbromal, Apronalide, Bomisovalum, Capuride, Carbromal and Ectylurea;

Alcohols such as Chlorhexadol, Ethchlorvynol, Meparfynol, 4-Methyl-5-thiazoleethanol, tert-Pentyl Alcohol and 2,2,2-Trichloroethanol;

Amides such as Butoctamide, Diethylbromoacetamide, Ibrotamide, Isovaleryl Diethylamide, Niaprazine, Tricetamide, Trimetozine, Zolpidem and Zopiclone;

Barbituric acid derivatives such as Allobarbital, Amobarbital, Aprobarbital, Barbital, Brallabarbital, Butabarbital Sodium, Butalbital, Butallylonal, Butethal, Carbubarb, Cyclobarbital, Cyclopentobarbital, Enallylpropymal, 5-Ethyl-5-(1-piperidyl) barbituric Acid, 5-Furfuryl-5-isopropylbarbituric Acid, Heptabarbital, Hexethal Sodium, Hexobarbital, Mephobarbital, Methitural, Narcobarbital, Nealbarbital, Pentobarbital Sodium, Phenallymal, Phenobarbital, Phenobarbital Sodium, Phenylmethylbarbituric Acid, Probarbital, Propallylonal, Proxibarbal, Reposal, Secobarbital Sodium, Talbutal, Tetrabarbital, Vinbarbital Sodium and Vinylbital;

Benzodiazepine derivatives such as Brotizolam, Doxefazepam, Estazolam, Flunitrazepam, Flurazepam, Haloxazolam, Loprazolam, Lormetazepam, Nitrazepam, Quazepam, Temazepam and Triazolam;

Bromides such as Ammonium Bromide, Calcium Bromide, Calcium Bromolactobionate, Lithium Bromide, Magnesium Bromide, Potassium Bromide and Sodium Bromide;

Carbamates such as Amyl Carbamate—Tertiary, Ethinamate, Hexaprpymate, Meparfynol Carbamate, Novonal and Tricholorourethan;

Chloral derivatives such as Carbocloral, Chloral Betaine, Chloral Formamide, Chloral Hydrate, Chloralantipyrine, Dichloralphenazone, Pentaerythritol Chloral and Triclofos;

Piperidinediones such as Glutehimide, Methyprylon, Piperidione, Pyrithyldione, Taglutimide and Thalidomide;

Quinazolone derivatives such as Etaqualone, Mecloqualone and Methaqualone; and others such as Acetal, Acetophenone, Aldol, Ammonium Valerate, Amphenidone, d-Bornyl α-Bromoisovalerate, d-Bornyl Isovalerate, Bromoform, Calcium 2-Ethylbutanoate, Carfinate, α-Chlorolose, Clomethiazole, Cypripedium, Doxylamine, Etodroxizine, Etomidate, Fenadiazole, Homofenazine, Hydrobromic Acid, Mecloxamine, Menthyl Valerate, Opium, Paraldehyde, Perlapine, Propiomazine, Rilmazafone, Sodium Oxybate, Sulfonethylmethane and Sulfonmethane.

135. Thrombolytic agents such as APSAC, Plasmin, Pro-Urokinase, Streptokinase, Tissue Plasminogen Activator and Urokinase;

136. Thyrotropic hormones such as TRH and TSH.

137. Uricosurics such as Benzbromarone, Ethebenecid, Orotic Acid, Oxycinchophen, Probenecid, Sulfinpyrazone, Ticrynafen and Zoxazolamine.

138. Vasodilators (cerebral) such as Bencyclane, Cinnarizine, Citicoline, Cyclandelate, Ciclonicate, Diisopropylamine Dichloractetate, Eburnamorine, Fenoxedil, Flunarizine, Ibudilast, Ifenprodil, Nafronyl, Nicametate, Nicergoline, Nimodipine, Papaverine, Pentifylline, Tinofedrine, Vincamine, Vinpocetine and Viquidil.

139. Vasodilators (coronary) such as Amotriphene, Bendazol, Benfurodil Hemisuccinate, Benziodarone, Chloacizine, Chromonar, Clobenfurol, Clonitrate, Dilazep, Dipyridamole, Droprenilamine, Efloxate, Erythritol, Erythrityl Tetranitrate, Etafenone, Fendiline, Floredil, Ganglefene, Hexestrol Bis(β-diethylaminoethyl ether), Hexobendine, Itramin Tosylate, Khellin, Lidoflazine, Mannitol Hexanitrate, Medibazine, Nicorandil, Nitroglycerin, Pentaerythritol Tetranitrate, Pentrinitrol, Perhexiline, Pimefylline, Prenylamine, Propatyl Nitrate, Pyridofylline, Trapidil, Tricromyl, Trimetazidine, Trolnitrate Phosphate and Visnadine.

140. Vasodilators (peripheral) such as Aluminum Nicotinate, Bamethan, Bencyclane, Betahistine, Bradykinin, Brovincamine, Bufoniode, Buflomedil, Butalamine, Cetiedil, Ciclonicate, Cinepazide, Cinnarizine, Cyclandelate, Diisopropylamine Dichloracetate, Eledoisin, Fenoxidil, Flunarisine, Heronicate, Ifenprodil, Inositol Niacinate, Isoxsuprine, Kallidin, Kallikrein, Moxisylyte, Nafronyl, Nicametate, Nicergoline, Nicofuranose, Nicotinyl Alcohol, Nylidrin, Pentifylline, Pentoxifylline, Piribedil, Protaglandin $E_1$, Suloctidil and Xanthinal Niacinate.

141. Vasoprotectants such as Benzarone, Bioflavonoids, Chromocarb, Clobeoside, Diosmin, Dobesilate Calcium, Escin, Rolescutol, Leucocyanidin, Metescufylline, Quercetin, Rutin and Troxerutin.

142. Vitamins, vitamin sources, and vitamin extracts such as Vitamins A, B, C, D, E, and K and derivatives thereof, Calciferols, Glycyrrhiza and Mecobalamin.

143. Vulnerary agents such as Acetylcysteine, Allantoin, Asiaticoside, Cadexomer Iodine, Chitin, Dextranomer and Oxaceprol.

144. Anticoagulants such as heparin.

145. Miscellaneous such as Erythropoietin (Hematinic), Filgrastim, Finasterlde (Benign Prostate Hypertrophy) and Interferon Beta 1—Alpha (Multiple Sclerosis).

The above list of active agents is based upon those categories and species of drugs set forth on pages THER-1 to THER-28 of *The Merck Index,* 12th Edition, Merck & Co. Rahway, N.J. (1996). This reference is incorporated by reference in its entirety.

The active agents contained in the bioadhesive composition can be in different forms depending on the solubility and release characteristics desired, such as neutral molecules, components of molecular complexes, and pharmaceutically acceptable salts, free acids or bases, or quaternary salts of the same, or as combinations of these. Simple derivatives of the drugs such as pharmaceutically acceptable ethers, esters, amides and the like which have desirable retention and release characteristics but which are easily metabolized at body pH, enzymes, pro-active forms, pro-drugs and the like can also be employed.

The active agent may comprise local anesthetic bases including weak organic bases which are lipophilic in nature and thus poorly soluble in water. However, such bases will typically react with organic or inorganic acids to form acidic, water-soluble acid addition salts. Thus, the term "base" when used with reference to an anesthetic agent means the un-ionized form of an anesthetic that can furnish an electron pair to form a covalent bond. The term "acid" when used with reference to an anesthetic agent means a substance that can take up an electron pair to form a covalent bond. The term "salt" when used with reference to an anesthetic agent means the form produced by an anesthetic base upon its reaction with an organic or inorganic acid.

Local anesthetic agents suitable for use in the practice of this invention include amides and esters. Examples of the amides are lidocaine, prilocaine, mepivacaine, bupivacaine, dibucaine and etidocaine. Esters include procaine, tetracaine, propoxycaine, chloroprocaine, benzocaine, butamben picrate, cocaine, hexylcaine, piperocaine, oxyprocaine and proparacaine. Other suitable local anesthetics for use in the practice of this invention include cyclomethycaine, dimethisoquin, ketocaine, diperodon, dyclonine and pramoxine, all typically administered in the form of the acid addition hydrochloride or sulfate salts.

The acid-addition salts of anesthetic agents suitable for the present invention include any non-toxic, pharmaceutically acceptable organic or inorganic salts which in certain embodiments are non-salicylate. Typical inorganic salts are the hydrogen halides, especially the hydrochlorides, carbonates, borates, phosphates, sulfates, hydrogen sulfates, hydrobromides, nitrates, sulfides, and arsenates. Typical organic salts are salts of mono- and polycarboxylic acids such as the citrate, tartrate, malate, cinnamate, oxalate, formate, succinate and phthalates. The base form and the salt form of a suitable anesthetic agent incorporated in the present composition should preferably be different anesthetic agents to achieve maximum duration of the combined anesthetic effect. The term "different" when used with reference to an anesthetic agent means that the salt form in any combination is not a salt of the base form used in the given combination.

In certain embodiments of this invention, the active agents comprise a free base local anesthetic agent that is selected from the group comprising lidocaine, procaine, propoxycaine, mepivacaine, prilocaine, dyclonine, pramoxine, benzocaine and chloroprocaine, in combination with the salt form of a different anesthetic agent. The salt form is preferably one selected from the group comprising prilocaine, tetracaine, bupivacaine, dyclonine, dibucaine, etidocaine and lidocaine salts.

In embodiments of this invention comprising a combination of both a free base form and a salt form of an anesthetic agent, the ratio of the free base form to the salt form in the composition will depend on several factors, namely: (1) the identity of the salt and base used; (2) the desired duration of action; and (3) the desired rapidity of anesthetic effect. As a general rule in the case of mucosal application, the ratios of base to salt are such that the free base form preferably should penetrate the mucosa and be at its peak effectiveness within about a 2 to 30 minute period, whereas, the salt form should preferably penetrate the mucosa and be at its peak effectiveness within a period of about 10 to 75 minutes. The duration of anesthesia will range from about 2 minutes to several hours, even up to 24 hours, depending on the base/salt combination selected and the length of application time. In practice to achieve this effect, the amount by weight of the base form will normally be in excess of the amount by weight of the salt form.

The term "onset of anesthesia" is intended to mean the time to obtain effect on the individual nerves. Onset of anesthesia principally depends upon the lipid solubility, molecular size, and quantity of available, un-ionized form of the local anesthetic. Thus, anesthetics with a high lipid solubility or a low $pK_3$, or both, have a more rapid onset of anesthesia.

The term "duration of anesthesia" as used herein means the period of time during which the local anesthetic measurably blocks nerve conduction. The foregoing depends upon all of the factors listed for onset of anesthesia, as well as on the extent of protein binding of the anesthetic agent.

An anesthetic agent free base can penetrate intact skin to a limited degree, and will more rapidly penetrate the skin if the keratin layers are abraded. In the case of mucosa, the anesthetic free base will penetrate much more readily due to the different keratin composition and the resulting difference in the hydrophilicity as compared to the *stratum corneum* of intact skin.

As a general rule, the salt forms of anesthetic agents do not appreciably penetrate intact skin, but the un-ionized base forms do penetrate to a limited degree. Both forms, salt and base, will penetrate abraded keratin layers. The salt form as well as the base form will penetrate, to a differing degree, mucosa due to the mucosa's hydrophilicity, as compared to the stratum corneum of intact skin. Generally, the higher the lipid content of the mucosal membrane, the more rapidly the base form of the anesthetic agent will be absorbed. Therefore, when the bioadhesive composition is used for application to buccal mucosa, the different lipid contents of the gum (gingiva) and the alveolar mucosa must be kept in mind in order to obtain the optimal penetration rate.

Although applicants do not intend to be bound by any theory or proposed mechanism of operation, it is believed that the base form of an anesthetic agent which is lipid soluble has a rapid onset of anesthesia since it enters the lipo-protein nerve membrane preventing the depolarization and ion exchange involved in stimulus conduction. On the other hand, the salt form of an anesthetic agent which is not lipid soluble, penetrates to the lipo-protein nerve membrane only after the buffering capacity of the skin or mucosal tissue converts the salt to the base, the final result being a delayed onset of anesthesia.

The salt forms of the anesthetic agents are selected on the basis of onset of anesthesia and duration of anesthesia. Adjusting the ratio of base to salt affects the relative onset as well as the duration of anesthesia. The greater the amount of anesthetic agent having a rapid onset of action, the shorter time to the onset of anesthesia. Similarly, the greater the amount of the anesthetic agent having a prolonged duration of anesthesia, the more prolonged the duration of anesthesia. Moreover, the composition can include other drugs used concomitantly.

Table 1 below summarizes the peak and duration of action of selected local anesthetics based primarily on application to skin or mucous membranes:

TABLE 1

| Local Anesthetic | Minimum Adult Dose | Maximum Adult Dose (mg) | Peak Effect (minutes) | Duration of Effect (minutes) |
| --- | --- | --- | --- | --- |
| Dibucaine | | 25 | <15 | 120–240 |
| Lidocaine | | 750 | 2–5 | 30–60 |
| Benzocaine | | 5000 | 1 | 30–60 |
| Cocaine | | 50 | 2–5 | 30–120 |
| Tetracaine | | 50 | 3–8 | 30–60 |
| Dyclonine | | 100 | <10 | <60 |
| Pramoxine | | 200 | 3–5 | NA |

NA: Not Available.
Source: Drug Facts and Comparisons, 1990 edition, J.B. Lippincott Company, St. Louis, MO. Page 601.

In general, the relative speed of the onset of anesthesia and duration of anesthesia for any given form of an anesthetic agent is available in the literature or can be calculated by standard tests for transmucosal dosage.

Onset time, as well as duration of anesthesia, will vary from individual to individual as well as on the basis of the site of application. When applying the composition to highly keratinized dermal tissues, the onset of anesthesia may take as long as 2 to 4 hours.

The term "therapeutically effective amount" as used herein with reference to the active agent is intended to mean the amount of active agent sufficient to produce the desired effect, local or systemic, when applied topically over the duration of intended use. The amounts necessary are known in the literature or may be determined by methods known in the art, but typically range from about 0.1 to about 20,000 mg, and preferably about 0.1 to about 1,000 mg, and most preferably range from about 0.1 to about 500 mg per human adult of about 75 kilograms body weight, depending on the active agents chosen and the site of application. The only upper limit on the amount of the active agent is that the composition should preferably be substantially free of crystals of the active agent and the amount of solvent used is not sufficient to undesirably affect the bioadhesive properties of the composition.

Therapeutic dosage and dosage unit amounts can be estimated by in vitro flux data using human cadaver skin or, alternatively, using animal skin as described in U.S. Pat. No. 4,751,087.

The concentration as well as the quantity of the active agent per unit area, namely per square or cubic centimeter, can be varied independently in order to achieve the desired therapeutic effect. For example, higher concentrations of anesthetic base contained in a dosage form of decreased thickness will result in an anesthetic with fast onset and short duration. High concentrations of the anesthetic base contained in a dosage form of increased thickness (higher mg of anesthetic per square or cubic centimeter) will result in potent anesthesia with fast onset and long duration. Low concentrations of the anesthetic base in a dosage form of decreased thickness will result in mild anesthesia with longer onset and short duration. Low concentrations of the anesthetic base contained in a dosage form of increased thickness will have mild anesthesia with longer onset and longer duration. As shown in the above explanation, the ability to vary the concentration of active agents from very low (about 1%) to high (40% or higher) of the total composition, when combined with the ability to coat thin (about 0.001 inches) or thick (about 0.500 or more inches) enables the practitioner of the invention to vary the dosage as needed for the particular site of topical application and therapeutic effects.

The bioadhesive compositions of the present invention may also contain one or more solvents or cosolvents. Such solvents and cosolvents are those known in the art, and are non-toxic, pharmaceutically acceptable substances, preferably liquids, which do not substantially negatively affect the bioadhesive properties or solubility of the active agents at the concentrations used. The solvent and cosolvent can be for the active agent or for the bioadhesive materials, or both. The solvent is preferably a polyhydric alcohol or combination of polyhydric alcohols. The solvent should include from about 5% to about 50%, and more preferably from about 10% to about 30% by weight of the dry weight of the total bioadhesive composition of a solvent known to plasticize the bioadhesive composition. Particularly useful plasticizers are glycols such as dipropylene glycol and propylene, fatty acids such as oleic acid and linoleic acid, fatty acid esters such as isopropyl myristate, vegetable, animal and fish oils such as hydrogenated castor oil, canola, cod liver, and lanolin, mineral oil, glycerine, lecithin, tocopherol and tocopheryl acetate. Alternatively, drugs which are liquid at room temperature, such as nitroglycerin, nicotine, selegiline and the like, may be used as plasticizers.

The use of a solvent (encompassing both solvents and plasticizers) has also been found to improve the appearance and texture of the finished composition, particularly for PVP and karaya gum embodiments. Specifically, the inclusion of a solvent in the bioadhesive composition is believed to cause the powdered karaya gum particles to swell or gel when added to a mixture or blend containing PVP, solvents and active agent (if the bioadhesive composition is not being used as a separate adhesive layer). When finished, the bioadhesive composition will have a softer, smoother finish than a bioadhesive composition which does not contain solvents. A bioadhesive composition which does not contain any solvents will generally have adequate wear properties and thus are not outside the scope of the present invention. However, the use of solvents is preferred for the reasons noted above.

The term "polyhydric alcohol" means any organic polyalcohol and includes dipropylene glycol, propylene glycol, polyethylene glycol, glycerin, butylene glycol, hexylene glycol, polyoxyethylene, polypropylene glycol, sorbitol, ethylene glycol, and the like. Other suitable solvents include fatty acids such as oleic acid, linoleic acid, capric acid and the like, polyethylene, polypropylene and ethers of fatty acids, as well as fatty esters or alcohols. Further suitable solvents include other non-toxic, non-volatile solvents commonly used in transdermal or transmucosal compositions for solubilizing active agents.

The above-mentioned polyhydric alcohols may include those having 2 to 6 alcoholic hydroxyl groups. Such polyhydric alcohols include glycols, triols and polyols having 4 to 6 alcoholic hydroxyl groups. Typical of said glycols are glycols containing 2 to 6 carbon atoms, e.g. ethylene glycol, propylene glycol, butylene glycol, polyethylene glycol (average molecular weight about 200–8,000, preferably about 200 to 6,000), etc. Examples of said triols include glycerin, trimethylolpropane, etc. Said polyols are exemplified by sorbitol (sorbit), polyvinylpyrrolidone, etc. These polyhydric alcohols may be used either singularly or in combination (preferably, of two or three). Thus, for example, glycerin or dipropylene glycol alone, or a mixture of either glycerin or dipropylene glycol with butylene glycol, can be employed.

Among those polyhydric alcohols, those which satisfy the requirements relevant to the adjustment and maintenance of softness of the external surface of the invention, the compatibility or co-dispersibility with the other components, and provide a proper consistency of the composition, may be freely used. Those which are low in volatility are generally preferred and, in this regard, dipropylene glycol, glycerin, propylene glycol, butylene glycol, and sorbitol are appropriate solvents, according to the invention.

Although the exact amount of the polyhydric alcohols, or fatty acids, esters, ethers or alcohols, that may be used in the composition depends on the nature and amount of other components, and therefore cannot be stated in general terms, the proportion may range up to about 30% by weight, and preferably from about 5% to about 20% by weight, and more preferably from about 5% to about 10% by weight based on the dry weight of the total bioadhesive composition.

The term "lsolubilized" is intended to mean that in the solvent, and subsequently the bioadhesive composition, there is an intimate dispersion of the active agent at the crystalline, molecular or ionic level, such that crystals of the active agent cannot be detected using a microscope having a magnification of 25x. As such, the active agent is termed herein to be in "non-crystallized" form when in the compositions of the present invention.

Generally, the concentration of solubilized pharmaceutically active agent can range from about 1% to about 50%, more preferably from about 2.5% to 40%, and optimally from about 5% to about 30% by weight of the dry weight of the total bioadhesive composition. In a preferred embodiment of the invention for topical administration of a single active agent, ketoprofen in the free acid form is used in a concentration between 2% and 30% by weight of dry weight of the total bioadhesive composition.

Generally, for topical administration of a combination of anesthetic agents, the ratio by weight of free base to the salt forms is about 90:10 to about 40:60, preferably about 75:25 to about 50:50, and more preferably about 70:30 to about 60:40. For other salts, the ratios are comparable based on relative molar amounts. Generally, the ratio by weight of base to salt is between about 1:2 to about 4:1. In a preferred embodiment of the invention for a combination of anesthetic agents, the ratio is about 2:1 base to salt, respectively, the base used is lidocaine and the salt used is a salt of prilocaine, bupivacaine, dyclonine, mepivacaine, or tetracaine, preferably the hydrochloride salt.

Higher concentrations of active agents, namely up to 50% by weight, can be achieved typically by mixing such agent (s) with an appropriate solvent, preferably at an elevated temperature, for example about 70 to 100° C., to obtain a mixture, preferably a solution, of the active agents which is then added to the bioadhesive materials. Omission of the solvent will typically yield a final composition filled with crystals or a crystalline mass.

Solvent selection for a combination of active agents depends on the form of the agent, inter alia, whether it is in free base, free acid, or acid-addition salt form.

Suitable solvents for the salt form of anesthetic agents are typically polar organic solvents. Polar organic solvents are preferably polyhydric alcohols, as discussed above. Suitable other solvents for either the free base or acid-addition form of anesthetic agents are those solvents known to dissolve either or both of these two types of forms including cyclic ketones such as 2-pyrrolidone; N-(2-hydroxyethyl) pyrrolidone, N-methylpyrrolidone, 1-dodecylazacycloheptan2-one and other n-substituted alkyl-azacycloalkyl-2-ones (azones) dimethylformadide, and dimethylsulfoxide. Other suitable solvents for the free base form of an anesthetic agent include cell envelope disordering compounds known to be useful in topical pharmaceutical preparations, which compounds are thought to assist in mucosal penetration by disordering the lipid structure of the stratum corneum cell-envelopes. Some of these compounds are generally encompassed by the formula:

wherein R is a straight-chain alkyl of about 7 to 16 carbon atoms, a non-terminal alkenyl of about 7 to 22 carbon atoms, or a branched-chain alkyl of from about 13 to 22 carbon atoms, and X is —OH, —COOCH$_3$, —COOC$_2$H$_5$, —OCOCH$_3$, —SOCH$_3$, —P(CH$_3$)$_2$O, —COOCH$_2$H$_4$OC$_2$H$_4$OH, —COOCH (CHOH)$_4$ CH$_2$OH, —COOCH$_2$CHOHCH3, —COOCH$_2$CH (OR")CH$_2$OR". —(OCH$_2$CH$_2$)$_m$OH, —COOR', or —CONR'$_2$ where R; is —H, —CH$_3$, —C$_2$H$_5$, —C$_3$H$_7$ OR —C$_2$H$_4$OH; R" is —H, or a non-terminal alkenyl of about 7 to 22 carbon atoms; and m is a positive integer from 2 to 6; provided that when R" is an alkenyl and X is —OH or —COOH, at least one double bond is in the cis-configuration.

The bioadhesive composition can also contain agents known to accelerate the delivery of the active agents through the skin or mucosa. These agents have been referred to as penetration or permeation enhancers, accelerants, adjuvants, and absorption promoters, and are collectively referred to as "enhancers."

Some examples of enhancers are monohydric alcohols such as ethanol and isopropyl, butyl and benzyl alcohols, or dihydric alcohols such as ethylene glycol, diethylene glycol, or propylene glycol dipropylene glycol and trimethylene glycol, or polyhydric alcohols such as glycerin, sorbitol and polyethylene glycol, which enhance drug solubility; polyethylene glycol ethers of aliphatic alcohols (such as cetyl, lauryl, oleyl and stearyl) including polyoxyethylene (4) lauryl ether, polyoxyethylene (2) oleyl ether and polyoxyethylene (10) oleyl ether commercially available under the trademark BRIJ® 30, 93 and 97 from ICI Americas, Inc., and BRIJ® 35, 52, 56, 58, 72, 76, 78, 92, 96, 700 and 721; vegetable, animal and fish fats and oils such as olive and castor oils, squalene, and lanolin; fatty acid esters such as propyl oleate, decyl oleate, isopropyl palmitate, glycol palmitate, glycol laurate, dodecyl myristate, isopropyl myristate and glycol stearate which enhance drug diffusibility; fatty acid alcohols such as oleyl alcohol and its derivatives; fatty acid amides such as oleamide and its derivatives; urea and urea derivatives such as allantoin which affect the ability of keratin to retain moisture; polar solvents such as dimethyldecylphosphoxide, methyloctylsulfoxide, dimethyllaurylamide, dodecylpyrrolidone, isosorbitol, dimethylacetonide, dimethylsulfoxide, decylmethylsulfoxide and dimethylformamide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the skin and drugs administered and esters of sorbitol and sorbitol anhydride such as polysorbate 20 commercially available under the trademark Tween® 20 from ICI Americas, Inc., as well as other polysorbates such as 21, 40, 60, 61, 65, 80, 81, and 85.

Other enhancers include oleic and linoleic acids, ascorbic acid, panthenol, butylated hydroxytoluene, tocopherol, tocopherol acetate, tocopheryl linoleate.

In one embodiment of the present invention, the bioadhesive composition comprises a mixture of at least one water-insoluble bioadhesive and at least one water soluble bioadhesive, an active agent, and a pharmaceutically acceptable solvent comprising a solvent known to plasticize the total bioadhesive composition.

In a preferred embodiment, the pharmaceutically acceptable solvent is in a preferred amount from about 20% to about 53% by weight based on the dry weight of the total composition, the plasticizer portion of which represents about 10% to 30% by weight based on the dry weight of the total composition, and the bioadhesive materials range in an amount from about 20% to about 55% by weight based on the dry weight of the total bioadhesive composition. More preferably, the bioadhesive composition of the present invention comprises about 10% to about 40% by weight of a polysaccharide bioadhesive, about 10% to about 40% by weight of a water soluble bioadhesive, about 10% to about 60% by weight of a solvent, and about 5% to about 40% by weight of an active agent, based on the dry weight of the total bioadhesive composition, and may further be comprised of a binder in an amount sufficient to bind the other ingredients. Preferred embodiments comprise a mixture of soluble PVP and another bioadhesive, preferably a natural gum.

In particular, it has unexpectedly been found that when karaya gum is employed as the polysaccharide bioadhesive and soluble PVP is employed as the water soluble bioadhesive, with a pharmaceutically acceptable solvent comprising a solvent known to plasticize the total bioadhesive composition, a bioadhesive composition that is also a pressure-sensitive adhesive is formed. This result is completely unexpected because neither karaya gum nor soluble PVP alone is a pressure-sensitive adhesive. The formation of a bioadhesive/pressure-sensitive adhesive composition is formed when karaya gum and PVP are employed at a ratio of between 1:10 and 10:1.

In general, the bioadhesive composition can have the following types and amounts of ingredients:

| Ingredient | Typical Range (% by weight) | Preferred Range (% by weight) | Optimum Range (% by weight) |
|---|---|---|---|
| Bioadhesive | 5 to 50 | 10 to 40 | 20 to 30 |
| PVP | 5 to 50 | 10 to 40 | 15 to 30 |
| Solvent | 5 to 70 | 10 to 60 | 20 to 53 |
| Active Agent | 1 to 50 | 2.5 to 40 | 5 to 30 |

The amount and type of PVP required in the preferred embodiments will depend on the quantity and type of drug present in the bioadhesive composition, as well as the type of bioadhesive, but can be readily determined through routine experimentation.

Typically, the PVP is present in an amount from about 5% to about 50% by weight, preferably from about 10% to about 40% by weight of the dry weight of the total bioadhesive composition. However, the amount of PVP can be higher than 20% for example, up to 40%, depending on the particular drug used and on the desired properties of the blend.

Said PVP preferably has a molecular weight of about 2,000 to 1,200,000, more preferably 5,000 to 100,000, and most preferably 7,000 to 54,000. PVP having a molecular weight of about 1,000,000 to about 1,500,000 is also preferred.

PVPs are sold to the pharmaceutical industry under the trademarks KOLLIDON by BASF AG, Ludwigshafen, Germany; PLASDONE, POLYPLASDONE and COPOLYMER 958 by ISP Technologies, Wayne, N.J. Preferred PVPs are KOLLIDON 12PF, 17PF, 25, 30, 90 and VA-64.

In another preferred embodiment of the invention, the bioadhesive composition includes a pressure-sensitive adhesive. The term "pressure-sensitive adhesive" as used herein refers to a viscoelastic material which adheres instantaneously to most surfaces with the application of very slight pressure and remains permanently tacky. A polymer is a pressure-sensitive adhesive within the meaning of the term as used herein if it has the properties of a pressure-sensitive adhesive per se or functions as a pressure-sensitive adhesive by admixture with tackifiers, plasticizers or other additives.

Suitable pressure-sensitive adhesives include all of the non-toxic natural and synthetic polymers known for or suitable for use in transdermal devices as hydrophobic adhesives including natural or synthetic elastomers, such as polyisobutylene, styrene, polybutadiene, styrene isoprene block copolymers, polyurethanes, polyacrylates, polysiloxanes and styrene/butadiene copolymers.

Particularly preferred pressure-sensitive adhesives are acrylic polymers, and more particularly solvent-based acrylic polymers. The term "acrylic polymer" is intended to be used interchangeably with the terms acrylate polymer, polyacrylate and polyacrylic adhesive polymers as used herein and as known in the art. The term "solvent-based" is used herein to mean substantially free of surfactants.

The acrylic polymers useful in practicing the invention are polymers of one or more monomers of acrylic acids and other copolymerizable monomers. The acrylic polymers also include copolymers of alkyl acrylates and/or methacrylates and/or copolymerizable secondary monomers or monomers with functional groups. By varying the amount of each type of monomer added, the cohesive properties of the resulting acrylic polymer can be changed as is known in the art. In general, the acrylic polymer is composed of at least 50% by weight of an acrylate or alkyl acrylate monomer, from 0 to 20% of a functional monomer copolymerizable with the acrylate, and from 0 to 40% of other monomers.

Acrylate monomers which can be used include acrylic acid, methacrylic acid, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, and tridecyl methacrylate.

Functional monomers, copolymerizable with the above alkyl acrylates or methacrylates, which can be used include acrylic acid, methacrylic acid, maleic acid, maleic anhydride, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate and methoxyethyl methacrylate and other monomers having at least one unsaturated double bond which participates in copolymerization reaction in one molecule and a functional group on its side chain such as a carboxyl group, a hydroxyl group, a sulfoxyl group, an amino group, an amido group and an alkoxyl, as well as a variety of other monomeric units including alkylene, hydroxy-substituted alkylene, carboxylic acid-substituted alkylene, vinylalkanoate, vinylpyrrolidone, vinylpyridine, vinylpirazine, vinylpyrrole, vinylimidazole, vinylcaprolactam, vinyloxazole, vinylacatate, vinylpropionate and vinylmorpholine.

Further details and examples of acrylic adhesives which are suitable in the practice of the invention are described in Satas, "Acrylic Adhesives," *Handbook of Pressure-Sensitive Adhesive Technology*, 2nd ed., pp. 396–456 (D. Satas, ed.), Van Nostrand Reinhold, New York (1989).

Suitable acrylic adhesives are commercially available and include the polyacrylate adhesives sold under the trademarks DURO-TAK by National Starch Company, Bridgewater, N.J.; GELVA by Monsanto, St. Louis, Mo.; HRJ by Schenectady International, Inc., Schenectady, N.Y.; MORSTIK by Morton International, Inc., Chicago, Ill.; and EUDRAGIT RL and RS by Roehm Pharma GmbH, Darmstadt, Federal Republic of Germany.

The amount of the pressure-sensitive adhesive used depends upon the concentration of active agent used to achieve a therapeutic affect. Typically, the pressure-sensitive adhesive is in an amount of about 10% to about 60% by weight of the dry weight of the total bioadhesive composition, and preferably about 15% to about 50%, and most preferably about 20% to about 40% by weight based on the dry weight of the total bioadhesive composition.

In yet a further embodiment of the present invention, the bioadhesive composition comprises from about 10% to about 60% by weight of a solvent-based acrylic polymer, from about 20% to about 50% by weight of a PVP polymer, from about 20% to about 53% by weight percent of at least one solvent, and from about 10% to about 25% by weight of an active agent, based on the dry weight of the total bioadhesive composition, and may further be comprised of a binder in an amount sufficient to bind the other ingredients. Again, the active agent desired for topical administration may be solubilized within the bioadhesive composition or may be administered separately.

In addition to the above ingredients, there may also be incorporated various pharmaceutically acceptable additives and excipients available to those skilled in the art. These additives include tackifying agents, which are particularly useful in those embodiments in which the active agent does not plasticize the bioadhesive composition, such as aliphatic hydrocarbons, mixed aliphatic and aromatic hydrocarbons, aromatic hydrocarbons, substituted aromatic hydrocarbons, hydrogenated esters, polyterpenes and hydrogenated wood rosins. Additional additives include binders such as lecithin which "binds" the other ingredients, or Theological agents (thickeners) containing silicone such as fumed silica, reagent grade sand, precipitated silica, amorphous silica, colloidal silicon dioxide, fused silica, silica gel, quartz and particulate siliceous materials commercially available as Syloid®, Cabosil®, Aerosil® and Whitelite®, for purposes of enhancing the uniform consistency or continuous phase of the final composition. Other additives and excipients include diluents, stabilizers, fillers, clays, buffering agents, biocides, humectants, anti-irritants, antioxidants, preservatives, flavoring agents, colorants, pigments and the like. Such additives or excipients are typically used in amounts up to 25% by weight of the bioadhesive composition, and preferably from about 0.1% to about 10% by weight.

The compositions according to the present invention can be prepared by mixing the one or more bioadhesives, in powder or liquid form, with the PVP and active agent, with or without a pressure-sensitive adhesive, preferably in an appropriate volatile, lower molecular weight solvent. When a pressure-sensitive adhesive is used, preferably the volatile, lower molecular weight solvent is an organic solvent supplied with the pressure-sensitive adhesive, for example, the acrylic adhesive. Typical liquids for use as such volatile solvents, as distinct from emulsion (typically aqueous) polymerization, singularly or in combination with other volatile and non-volatile solvents, are volatile polar and non-polar organic liquids such as lower molecular weight alkanols (e.g., isopropanol and ethanol), aromatics such as benzene derivatives (e.g., xylene and toluene), lower molecular weight alkanes and cycloalkanes (e.g., hexane, heptane and cyclohexane) and alkanoic acid ester such as ethyl or butyl acetate.

Preferably, the mixture is cast at ambient temperature and pressure followed by evaporation of the volatile solvents, for example, by evaporation at slightly elevated temperatures, to form the bioadhesive blend. The non-volatile or higher boiling point solvents such as the polyols used in the composition remain therein.

An individual unit or device (often referred to as a "delivery system") comprising the present invention can be prepared in any manner known to those of skill in the art. An exemplary general method of preparation is as follows:

1. Appropriate amounts of the PVP polymer, pressure-sensitive adhesive(s), solvent(s) and/or co-solvent(s), enhancer(s), additive(s) and excipient(s) are combined and thoroughly mixed together in a vessel.

2. The one or more active agents are then added to the mixture and agitation is carried out until the agent(s) are uniformly mixed therein, if the bioadhesive composition is being used as both the adhesive and the active agent source. Otherwise, no active agent is added.

3. Appropriate amounts of other bioadhesive material(s), such as kayara gum, may be then added to the active agent containing mixture, and thoroughly mixed.

4. The composition is then transferred to a coating operation where it is coated onto a release liner at a controlled specified thickness. The coated composition is then passed through an oven in order to drive off all volatile processing solvents.

5. The composition coated on the release liner is then brought into contact with a backing (layer) and wound into rolls.

6. Appropriate size and shape delivery systems are die-cut from the roll material and then pouched.

The order of steps, the amount of the ingredients, and the amount and time of agitation or mixing may be important process variables which will depend on the specific polymers, active agents, solvents and/or cosolvents, enhancers and additives and excipients used in the composition. These factors can be adjusted by those skilled in the art, while keeping in mind the objects of achieving a solubilized active agent and providing a uniform product. It is believed that a number of other methods, for example, other methods of coating backings that are well-known in the art such as Mayer rod, gravure, knife-over roll, extrusion, casting, calendaring and molding, or changing the order of certain steps, for example, in one embodiment, anesthetic agents are dissolved in a solvent, preferably a polyhydric alcohol, and then the resulting mixture is added to the other bioadhesive components prior to coating, can be carried out and will also give desirable results.

The present inventors have found, however, that by adding the non-PVP bioadhesive, such as kayara gum, to a mixture containing the PVP and solvents, the finished bioadhesive composition will have a smoother, softer finish.

The backing layer, typically occlusive to water permeation, serves to retain and maintain the bioadhesive composition disposed thereon in a defined size and shape, prevent loss of the active agent and/or enhancers to the environment, render the individual unit or delivery system (in conjunction with the release liner) transportable, and generally provide protection both prior to and after application of the unit or system to a subject.

Suitable materials that can be used, singularly, in combination, as laminates or as coextrusions, to form the backing layer are well known in the art and include films or sheets of polyethylene, polyester, polypropylene, polyurethane, polyolefin, polyvinyl alcohol, polyvinyl chloride, polyvinylidene, polyamide, vinyl acetate resins, BAREX®, ethylene/vinyl acetate copolymers, ethylene/ethylacrylate copolymers, metal-vapor deposited films or sheets thereof, rubber sheets or films, expanded synthetic resin sheets or films, non-woven fabrics, fabrics, knitted fabrics, clothes, foils and papers.

The backing layer generally has a thickness in the range of 2 to 1000 micrometers and the bioadhesive composition is generally disposed on the backing layer in a thickness ranging from about 12 to 250 micrometers. The backing layer may be pigmented, for example colored to either match with or conversely easily distinguish from the site of application, and/or contain printing, labeling and other means of identification and/or tracability of the unit or system itself. The backing layer may further be made opaque or substantially opaque (i.e., preventing light or certain energy wavelengths from penetrating or passing through), such as by metallization, fillers, inks, dyes and the like, for purposes of protecting photosensitive active agents, such as ketoprofen, from degradation and/or preventing photoallergic reactions or irritations on the subject.

The release liner or peel strip is also intended to prevent loss of the active agent and/or enhancers to the environment, and render the individual unit or delivery system (in conjunction with the backing layer) transportable, as well as generally protect the bioadhesive composition from contamination and the like until its application to a subject. The release liner is typically also impermeable and occlusive, and must be compatible with the particular bioadhesives and/or active agents so as not to interfere with their ultimate topical application and therapeutic effect.

Suitable materials that can be used, singularly, in combination, as laminates or as coextrusions, to form the release liner are also well known in the art and include any material suitable for the backing layer. When the release liner is composed of a material which typically does not readily release (i.e., is not easily removed or separated from the bioadhesive composition), for example paper, a coating material such as a silicone may be applied to the release liner by any conventional means. Preferred release liners are films commercially available from DuPont, Wilmington, Del., under the trademark Mylare, and fluropolymer (silicone) coated films commercially available from Rexam Release, Oak Brook, Ill. under the trademark FL2000® and MRL2000, and from 3M Corporation, St. Paul, Minn. under the trademark ScotchPak® 1022.

The configuration of an individual unit or delivery system of the present invention can be in any shape, preferably a defined geometric shape, and size (i.e., surface area of application) as is necessary or desirable. The shape is achieved by conventional techniques, for example, cutting or punching, and such techniques are described, for example, in U.S. Pat. Nos. 5,032,207, 5,405,486 and 5,656,285. The intended site of application is an important factor in determining the size and shape of an individual unit or delivery system of the present invention, and can be adjusted by those skilled in the art as is necessary to effect therapy. Typically the size should not exceed 100 cm$^2$. Preferred sizes range from about 0.1 cm$^2$ to about 60cm$^2$, and more preferred range from about 1.5 cm$^2$ to about 30cm$^2$, and optimally from about 2.0 cm$^2$ to about 10cm$^2$.

The bioadhesive compositions of the present invention preferably comprise the active agents solubilized therein, and attach directly to the skin or mucosa after removal of the release liner.

Alternatively, the bioadhesive composition may be utilized, without an active agent, in a multi-layer delivery system as an "underlay" adhesive layer (i.e., attaches directly to the skin or mucosa after removal of the release liner) in which the active agent is solubilized or contained in one or more other separate layers, and which other layers may or may not comprise embodiments of the bioadhesive compositions of the present invention.

In yet another aspect, the bioadhesive composition of the present invention may be utilized, without an active agent, in a reservoir-type delivery system as an underlay adhesive or a peripheral adhesive layer or ring, in which the active agent is solubilized or contained in a separate reservoir or depot, and which reservoir or depot may or may not comprise embodiments of the bioadhesive compositions of the present invention.

If the bioadhesive composition is used as an adhesive ring around the active agent reservoir or drug depot, the bioadhesive layer is peripheral to the active agent reservoir. If the bioadhesive composition is used as a separate underlying adhesive layer to the layer containing the active agent, the adhesive layer is adjacent to and in contact with a first major surface of the active agent layer. The composition may then include a backing layer which is in contact with a second major surface of the active agent layer which is opposite the first major surface of the active agent layer; and a removable release liner which is in contact with a second major surface of the adhesive layer which is opposite to the first major surface of the active agent layer.

If the bioadhesive layer is used without an active agent as a separate underlying layer, the thickness of the underlying layer is generally in the range of 1 to 10 mils thick, more preferably 2 to 8 mils, and most preferably 4 to 6 mils thick.

One especially preferred embodiment for the bioadhesive composition includes: soluble PVP; a polysaccharide, preferably a natural gum, more preferably kayara gum; a separate plasticizer, which is preferably glycerin; a separate solvent, which is preferably a polyhydric alcohol, more preferably propylene glycol; and one or more active agents if the active agent source is not separate from the bioadhesive composition.

The amounts of each component (active agent is not included) in weight % based on the combined dry weight of the at least one soluble polyvinylpyrrolidone polymer, the kayara gum, the polyhydric alcohol and the glycerin is shown below:

| Ingredient | Typical Range (% by weight) | Preferred Range (% by weight) | Optimum Range (% by weight) |
|---|---|---|---|
| Kayara gum | 10 to 50 | 20 to 40 | 25 to 35 |
| PVP | 5 to 30 | 7 to 15 | 9 to 13 |
| Propylene Glycol | 7 to 40 | 15 to 35 | 25 to 30 |
| Glycerin | 10 to 50 | 20 to 40 | 25 to 35 |

If the bioadhesive composition contains the one or more active agents, the amounts of the foregoing components may be adjusted by those skilled in the art depending on the amount and type of the one or more active agents.

A preferred weight ratio of kayara gum to glycerin is of from 10:1 to 1:2, more preferably about 1:1. A preferred weight ratio of kayara gum to propylene glycol is of from 10:1 to 1:1, more preferably about 1:0.8. A preferred weight ratio of the PVP to kayara gum is of from 1:1 to 1:7, preferably 1:3 to 1:4.

It has been found that if the especially preferred composition in the table above is used as a separate adhesive layer, then the composition is capable of decreasing the time required for adhesion of a composition to mucosal tissue to such an extent that the composition adheres to the mucosal tissue substantially at the moment of contact with no additional pressure.

The following examples will further describe the instant invention, and are used for the purposes of illustration only, and should not be considered as limiting in any way the invention being disclosed herein.

Percent (%) as used in Example 1 refers to percentage of the liquid formulation on a weight to weight basis and temperatures are given in degrees celsius (° C.)

Example 1

| Ingredient | % (w/w) |
|---|---|
| Bioadhesive (karaya gum) | 21 |
| Polyvinylpyrrollidone | 11 |
| Solvent (propylene glycol) | 7 |
| Solvent (glycerin) | 19 |
| Anesthetic agent base (lidocaine base) | 28 |
| Anesthetic agent salt (prilocaine hydrochloride) | 14 |

The final product is manufactured by first blending the lidocaine base, prilocaine hydrochloride, propylene glycol, PVP and glycerin at about 70 to 90° C. until all of the drug is dissolved. The solution is then cooled to 20 to 35° C. prior to adding the karaya gum. Once the karaya gum is added, the final composition is applied to a suitable backing material such as a non-woven, polyester film (for example, the film sold under the trademark Sontara 8100, manufactured by DuPont de Nemours, E. I. and Co., Wilmington, Del.) and warmed to about 100° C. to accelerate the formation into its final, finite form.

EXAMPLE 1a

In example 1a, a composition is prepared as followed without a drug. The composition can be then be used alone as an underlay adhesive layer, or an active agent can be added, prior to removal of volatile processing solvents.

| Ingredient | w/w % (dry) |
|---|---|
| Bioadhesive (karaya gum) | 31.4 |
| Polyvinylpyrrollidone (Kollidon K90) | 10.4 |
| Solvent (propylene glycol) | 26.8 |
| Plasticizer (glycerin) | 31.4 |

EXAMPLE 2

A bioadhesive composition is prepared by combining 20.59% w/w wet of karaya gum, 10.59% w/w wet of soluble PVP (PLASDONE K90), 7.94% w/w wet of oleic acid, 45.0% w/w of ethanol and 15.88% w/w wet of ketoprofen in an appropriate container, and mixing thoroughly until the mixture is complately homogeneous. The resulting composition has the ingredient concentrations on a dry weight basis, that is, after removal of the volatile process solvent (ethanol).

EXAMPLE 2

| COMPONENT | PERCENT BY WEIGHT |
|---|---|
| Bioadhesive (Karaya Gum) | 35.36 |
| Polyvinylpyrrolidone (PLASDONE K90) | 19.19 |
| Oleic Acid | 15.15 |
| Ketoprofen | 30.30 |
| | 100.00 |

In the following examples, the method of Example 2 is used with the appropriate amounts of starting materials to yield compositions having the following ingredient concentrations, on a weight percent by dry weight of the total bioadhesive composition. Volatile solvents, where indicated by ( ), are not present in the final composition.

Moreover, the drugs in examples 21–29 are dispersed in the final composition rather than solubilized.

| | EXAMPLES | | | | | |
|---|---|---|---|---|---|---|
| COMPONENT | 3 | 4 | 5 | 6 | 7 | 8 |
| Bioadhesive (Karaya Gum) | 40 | 40 | 35 | 45 | 40 | 40 |
| Polyvinylpyrrolidone (Kollidon ® 12PF) | 30 | 0 | 0 | 0 | 0 | 0 |
| Polyvinylpyrrolidone (Kollidon ® 17) | 0 | 25 | 0 | 0 | 0 | 0 |
| Polyvinylpyrrolidone (Kollidon ® 30) | 0 | 0 | 30 | 0 | 0 | 0 |
| Polyvinylpyrrolidone (Kollidon ® 90) | 0 | 0 | 0 | 20 | 0 | 20 |
| Vinypyrrolidone/Vinyl Acetate (Kollidon ® VA64) | 0 | 0 | 0 | 0 | 25 | 0 |
| Oleic Acid | 10 | 15 | 15 | 15 | 15 | 15 |
| Ketoprofen | 20 | 20 | 20 | 20 | 20 | 20 |
| Lidocaine (base) | 0 | 0 | 0 | 0 | 0 | 5 |
| Volatile Solvent (Ethanol) | (75) | (75) | (85) | (100) | (85) | (100) |

| | EXAMPLES | | |
|---|---|---|---|
| COMPONENT | 9 | 10 | 11 |
| Bioadhesive (Karaya Gum) | 25 | 35 | 35 |
| Polyvinylpyrrolidone (Plasdone ® K90) | 25 | 20 | 20 |
| Linoleic Acid | 10 | 0 | 25 |
| 1,3 Butylene Glycol | 10 | 25 | 0 |
| Lidocaine (base) | 20 | 0 | 0 |
| Bupivicaine (base) | 0 | 20 | 0 |
| Bupivicaine (salt) | 10 | 0 | 20 |
| Ethanol | (100) | (100) | (100) |

| | EXAMPLES | | |
|---|---|---|---|
| COMPONENT | 12 | 13 | 14 |
| Bioadhesive (Karaya Gum) | 32 | 0 | 0 |
| Soy Polysaccharide (Emcosoy ® 50) | 0 | 0 | 50 |
| Vinylpyrrolidone/Vinyl Acetate (Kollidon ® VA64) | 28 | 40 | 0 |
| Polyvinylpyrrolidone (Plasdone ® K90) | 0 | 0 | 25 |
| Alginic Acid NF (Satialgine ™ H8) | 0 | 32 | 0 |
| Dipropylene glycol | 20 | 18 | 0 |
| Oleic Acid | 0 | 0 | 15 |
| Sodium Diclofenac | 20 | 10 | 0 |
| Diclofenac (acid) | 0 | 0 | 10 |
| Ethanol | 0 | 0 | (60) |
| Ethyl Acetate | (45) | (75) | 0 |

| | EXAMPLES | | |
|---|---|---|---|
| COMPONENT | 15 | 16 | 17 |
| Bioadhesive (Karaya Gum) | 30 | 35 | 0 |
| Polyvinyl Acetate (Sentry ® Plus PVAc 12) | 35 | 0 | 0 |
| Polyvinyl Acetate (Sentry ® Plus PVAc 40) | 0 | 35 | 40 |
| Alginic Acid NF (Satialgine ™ H8) | 0 | 0 | 30 |
| Propylene Glycol | 0 | 20 | 20 |
| Oleic Acid | 15 | 0 | 0 |
| Ketoprofen | 20 | 0 | 0 |
| Sodium Diclofenac | 0 | 10 | 0 |
| Sodium Naproxen | 0 | 0 | 10 |
| Ethyl Acetate | (50) | (60) | (60) |

| | EXAMPLES | | |
|---|---|---|---|
| COMPONENT | 18 | 19 | 20 |
| Bioadhesive (Karaya Gum) | 6 | 10 | 12 |
| Vinylpyrrolidone/Vinyl Acetate (ISP COPOYMER 958) | 70 | 71 | 0 |
| Vinyl pyrrolidone/Dimethylaminoethylmethacrylate (ISP COPOLYMER 5630) | 0 | 0 | 64 |
| Oleyl Alcohol | 6 | 6 | 6 |
| Depropylene Glycol | 8 | 8 | 8 |
| Testosterone | 10 | 0 | 0 |
| Methyl Testosterone | 0 | 5 | 0 |
| Testosterone Acetate | 0 | 0 | 10 |
| Ethanol | 0 | 0 | (100) |

|  | EXAMPLES | | | | | | | |
|---|---|---|---|---|---|---|---|---|
| COMPONENT | 21 | 22 | 23 | 24 | 25 | 26 | 27 | 28 |
| Bioadhesive (Kayara Gum) | 0 | 0 | 0 | 0 | 0 | 0 | 0 | 29.9 |
| Soy Polysaccharide (Emcosoy ® 50) | 0 | 0 | 0 | 0 | 0 | 0 | 4.9 | 0 |
| Ethyl Cellulose (Ethocel ® 4) | 0 | 24 | 0 | 9.9 | 37.9 | 0 | 0 | 0 |
| Polyvinylpyrrolidone (Kollidon ® 90) | 0 | 0 | 25 | 60 | 60 | 30 | 0 | 45 |
| Vinylpyrrolidone/Vinyl Acetate (Kollidon ® VA64) | 40 | 50 | 0 | 0 | 0 | 0 | 0 | 0 |
| Polyvinyl Acetate (Sentry ® Plus PVAc12) | 0 | 0 | 0 | 0 | 0 | 0 | 40 | 0 |
| Ethyl Cellulose (Ethocel ® 10) | 19 | 0 | 0 | 0 | 0 | 0 | 25 | 0 |
| Ethyl Cellulose (Ethocel ® 100) | 0 | 0 | 14 | 0 | 0 | 19.9 | 0 | 0 |
| Oleic Acid | 40 | 25 | 60 | 0 | 0 | 0 | 30 | 25 |
| Polyoxyethylene (2) Oleyl Ether (BRIJ ® 93) | 0 | 0 | 0 | 2 | 2 | 0 | 0 | 0 |
| 1,3 Butylene Glycol | 0 | 0 | 0 | 28 | 0 | 50 | 0 | 0 |
| Insulin | 1 | 1 | 1 | 0.1 | 0 | 0 | 0 | 0 |
| [Arg$^8$] Vassopressin | 0 | 0 | 0 | 0 | 0.1 | 0 | 0.1 | 0 |
| Calatonin | 0 | 0 | 0 | 0 | 0 | 0.1 | 0 | 0.1 |
| Ethyl Acetate | (100) | (100) | (150) | (200) |  | (100) | (100) | (75) |
| Acetone | 0 | 0 | 0 | 0 | (200) | 0 | 0 | 0 |

|  | EXAMPLES | | | | | | | |
|---|---|---|---|---|---|---|---|---|
| Component | 29 | 30 | 31 | 32 | 33 | 34 | 35 | 36 |
| Ethylcellulose (Ethocel ® 7) | 36.5 | 36.5 | 32.9 | 33.0 | 29.4 | 29.4 | 0 | 0 |
| Ethylcellulose (Ethocel ® 4) | 0 | 0 | 0 | 0 | 0 | 0 | 33.0 | 36.7 |
| Bioadhesive (Karaya Gum) | 13.1 | 9.8 | 13.2 | 16.5 | 19.9 | 19.9 | 13.2 | 13.1 |
| Polyvinylpyrrolidone (Kollidon ® 30) | 3.4 | 3.4 | 6.9 | 3.4 | 3.4 | 3.5 | 6.9 | 0 |
| Polyvinylpyrrolidone (Kollidon ® 90) | 10.5 | 13.9 | 10.4 | 10.5 | 10.5 | 10.5 | 10.4 | 10.4 |
| Dipropylene Glycol | 7.3 | 7.3 | 7.3 | 7.3 | 7.4 | 7.4 | 7.3 | 7.2 |
| Propylene Glycol | 11.0 | 11.0 | 11.0 | 11.0 | 11.0 | 11.0 | 11.0 | 11.0 |
| Ketoprofen | 18.2 | 18.1 | 18.3 | 18.3 | 18.4 | 18.3 | 18.2 | 18.1 |
| Polyethylene Oxide (WSRN 750) | 0 | 0 | 0 | 0 | 0 | 0 | 0 | 3.5 |

|  | EXAMPLE | | | | | | |
|---|---|---|---|---|---|---|---|
| Component | 37 | 38 | 39 | 40 | 41 | 42 | 43 |
| Ketoprofen | 10 | 10 | 10 | 10 | 10 | 10 | 10 |
| Dipropylene Glycol | 4.5 | 4.5 | 4.5 | 4.5 | 4.5 | 4.5 | 4.5 |
| Propylene Glycol | 4.5 | 4.5 | 4.5 | 4.5 | 4.5 | 4.5 | 4.5 |
| Phosphatidylcholine (Lecithin PG) | 29 | 29 | 29 | 29 | 29 | 29 | 29 |
| Polyvinylpyrrolidone (Kollidon ® 12PF) | 4.5 | 0 | 0 | 0 | 0 | 0 | 0 |
| Polyvinylpyrrolidone (Kollidon ® 17PF) | 0 | 4.5 | 0 | 0 | 0 | 0 | 0 |
| Polyvinylpyrrolidone (Kollidon ® 30) | 0 | 0 | 4.5 | 0 | 0 | 0 | 0 |
| Polyvinylpyrrolidone (Kollidon ® CL-M) | 0 | 0 | 0 | 4.5 | 0 | 0 | 0 |
| Vinylpyrrolidone/ Vinyl Acetate (Kollidon ® VA64) | 0 | 0 | 0 | 0 | 4.5 | 0 | 0 |
| Acrylic Adhesive (Eudragit ® L100) | 0 | 0 | 0 | 0 | 0 | 4.5 | 0 |
| Lactose Povidone (Crospovidone Blend) (Ludipress ®) | 0 | 0 | 0 | 0 | 0 | 0 | 4.5 |
| Glycerin | 18.5 | 18.5 | 18.5 | 18.5 | 18.5 | 18.5 | 18.5 |
| Bioadhesive (Karaya Gum) | 29 | 29 | 29 | 29 | 29 | 29 | 29 |

| Component | EXAMPLES | | | | | | | | |
|---|---|---|---|---|---|---|---|---|---|
| | 44 | 45 | 46 | 47 | 48 | 49 | 50 | 51 | 52 |
| Cellulose Acetate | 25.6 | 15.5 | 11.0 | 10.9 | 15.5 | 9.4 | 0 | 0 | 0 |
| Bioadhesive (Karaya Gum) | 16.1 | 18.6 | 19.8 | 19.6 | 18.6 | 17.0 | 22.0 | 17.0 | 18.8 |
| Polyvinylpyrrolidone (Kollidon ® 30) | 0 | 0 | 9.9 | 21.7 | 20.6 | 17.9 | 23.2 | 17.2 | 19.8 |
| Ethylcellulose (Ethocel ® 7) | 0 | 0 | 0 | 0 | 0 | 14.2 | 0 | 18.9 | 20.8 |
| Dipropylene Glycol | 22.4 | 25.8 | 27.5 | 27.2 | 25.8 | 23.6 | 30.5 | 18.9 | 20.8 |
| Ketoprofen | 18.0 | 21.5 | 21.9 | 20.6 | 19.5 | 17.9 | 24.3 | 28.0 | 19.8 |
| Polyvinylpyrrolidone (Kollidon ® 90) | 17.9 | 18.6 | 9.9 | 0 | 0 | 0 | 0 | 0 | 0 |

| Component | EXAMPLES | | |
|---|---|---|---|
| | 53 | 54 | 55 |
| Ketoprofen | 19 | 20 | 19 |
| Polyvinylpyrrolidone (Kollidon ® 90) | 6 | 6 | 0 |
| Polyvinylpyrrolidone (Kollidon ® 30) | 0 | 0 | 4 |
| Polyvinylpyrrolidone (Kollidon ® CL-M) | 0 | 0 | 6 |
| Ethyl Cellulose (Ethocel ® 7) | 4 | 0 | 0 |
| Propylene Glycol | 8 | 8 | 10 |
| Phosphatidylcholine (Lecithin PG) | 21 | 22 | 19 |
| Glycerin | 14 | 15 | 14 |
| Bioadhesive (Karaya Gum) | 28 | 29 | 28 |

| Component | EXAMPLES | | | |
|---|---|---|---|---|
| | 63 | 64 | 65 | 66 |
| Lidocaine (Base) | 20 | 20 | 20 | 20 |
| Bupivacaine HCL | 10 | 10 | 10 | 10 |
| Phosphatidylcholine (Lecithin PG) | 21 | 21 | 20 | 20 |
| Dipropylene Glycol | 5 | 0 | 5 | 5 |
| Propylene Glycol | 0 | 5 | 0 | 0 |
| Glycerin | 16 | 12 | 17 | 15 |
| Bioadhesive (Karaya Gum) | 23 | 27 | 23 | 25 |
| Acrylic Adhesive (Eudragit L100) | 5 | 5 | 0 | 0 |
| Polyvinylpyrrolidone (Kollidon ® CL-M) | 0 | 0 | 5 | 0 |
| Vinylpyrrolidone/Vinyl Acetate (Kollidon ® VA64) | 0 | 0 | 0 | 5 |

| Component | EXAMPLE | | | | | | |
|---|---|---|---|---|---|---|---|
| | 56 | 57 | 58 | 59 | 60 | 61 | 62 |
| Ketoprofen | 11 | 11 | 11 | 11 | 11 | 11 | 11 |
| Phosphatidylcholine (Lecithin PG) | 25 | 24 | 24 | 24 | 34 | 33 | 25 |
| Propylene Glycol | 9 | 9 | 12 | 9 | 0 | 0 | 9 |
| Acrylic Adhesive (Eudragit ® L100) | 3 | 3 | 0 | 0 | 3 | 3 | 0 |
| Polyvinylpyrrolidone (Kollidon ® CL-M) | 0 | 3 | 3 | 6 | 0 | 0 | 0 |
| Vinylpyrrolidone/Vinyl Acetate (Kollidon ® VA64) | 0 | 0 | 0 | 0 | 0 | 3 | 3 |
| Bioadhesive (Karaya Gum) | 32 | 32 | 32 | 32 | 33 | 32 | 33 |
| Glycerin | 19 | 18 | 18 | 18 | 19 | 18 | 19 |

| Component | EXAMPLES | | | | | |
|---|---|---|---|---|---|---|
| | 67 | 68 | 69 | 70 | 71 | 72 |
| Ketoprofen | 29 | 29 | 29 | 29 | 29 | 29 |
| Bioadhesive (Karaya Gum) | 37 | 32 | 27 | 27 | 27 | 27 |
| Polyvinylpyrrolidone (Plasdone ® 90) | 19 | 19 | 19 | 19 | 19 | 19 |
| Oleic Acid | 15 | 20 | 14 | 14 | 14 | 14 |
| Acrylic Adhesive (Duro-Tak ® 87-2353) | 0 | 0 | 11 | 0 | 0 | 0 |
| Polyisobutylene (Vistannex LMMS) | 0 | 0 | 0 | 11 | 0 | 0 |
| Polyisobutylene (Vistannex LMMH) | 0 | 0 | 0 | 0 | 11 | 0 |
| Rubber-Based Adhesive (Morstik ® 103) | 0 | 0 | 0 | 0 | 0 | 11 |

| Component | EXAMPLES | | | | | | | | | | | | |
|---|---|---|---|---|---|---|---|---|---|---|---|---|---|
| | 73 | 74 | 75 | 76 | 77 | 78 | 79 | 80 | 81 | 82 | 83 | 84 | 85 |
| Lidocaine (Base) | 20 | 20 | 20 | 20 | 0 | 0 | 0 | 0 | 0 | 20 | 19 | 20 | 20 |
| Ketoprofen | 0 | 0 | 0 | 0 | 20 | 0 | 0 | 0 | 0 | 0 | 0 | 0 | 0 |
| Diclofenac (Acid) | 0 | 0 | 0 | 0 | 0 | 0 | 0 | 0 | 8 | 8 | 0 | 0 | 0 |
| Diclofenac (Sodium) | 0 | 0 | 0 | 0 | 0 | 0 | 0 | 12 | 12 | 0 | 0 | 0 | 0 |
| Dipropyleneglycol | 13 | 8 | 8 | 8 | 8 | 10 | 7 | 8 | 8 | 0 | 0 | 0 | 0 |
| Bioadhesive (Karaya Gum) | 29 | 29 | 29 | 29 | 29 | 37 | 35 | 29 | 28 | 29 | 28 | 29 | 29 |
| Polyvinylpyrrolidone (Kollidon ® 30) | 0 | 0 | 0 | 0 | 0 | 0 | 0 | 0 | 0 | 0 | 0 | 0 | 5 |
| Polyvinylpyrrolidone (Kollidon ® 90) | 0 | 5 | 0 | 0 | 5 | 6 | 6 | 5 | 5 | 0 | 5 | 0 | 0 |
| Polyvinylpyrrolidone (Kollidon ® CM) | 0 | 0 | 5 | 0 | 0 | 0 | 0 | 0 | 0 | 0 | 0 | 0 | 0 |
| Acrylic Adhesive (Eudragit ® RS100) | 0 | 0 | 0 | 0 | 0 | 0 | 7 | 0 | 5 | 0 | 5 | 0 | 0 |

-continued

| | EXAMPLES | | | | | | | | | | | | |
|---|---|---|---|---|---|---|---|---|---|---|---|---|---|
| Component | 73 | 74 | 75 | 76 | 77 | 78 | 79 | 80 | 81 | 82 | 83 | 84 | 85 |
| Lactose Povidone (Crespovidone Blend) (Lupipress ®) | 0 | 0 | 0 | 5 | 0 | 0 | 0 | 0 | 0 | 0 | 0 | 0 | 0 |
| Phosphatidylchaline (Lecithin PG) | 22 | 22 | 22 | 22 | 22 | 28 | 26 | 22 | 20 | 22 | 21 | 22 | 22 |
| Glycerin | 16 | 16 | 16 | 16 | 16 | 19 | 19 | 16 | 14 | 16 | 16 | 16 | 16 |
| Ethylcellulose (Ethocel ® 7) | 0 | 0 | 0 | 0 | 0 | 0 | 0 | 0 | 0 | 0 | 0 | 0 | 0 |
| Propylene Glycol | 0 | 0 | 0 | 0 | 0 | 0 | 0 | 0 | 0 | 13 | 8 | 13 | 8 |

What is claimed is:

1. A bioadhesive composition in a flexible, finite form for topical application on mucous membranes of one or more active agents resulting from an admixture which comprises:
    (a) at least one soluble polyvinylpyrrolidone polymer (PVP);
    (b) at least one bioadhesive;
    (c) a therapeutically effective amount of one or more active agents;
    (d) a backing layer which is occlusive to the active agents; and
    (e) optionally one or more solvents, wherein the composition is substantially free of water.

2. A composition as claimed in claim 1, wherein the bioadhesive comprises a polysaccharide.

3. A composition as claimed in claim 1, wherein the bioadhesive comprises a natural gum.

4. A composition as claimed in claim 1, wherein the bioadhesive comprises karaya gum.

5. A composition as claimed in claim 1, wherein the one composition includes one or more solvents.

6. A composition as claimed in claim 5, wherein the one or more solvents includes a separate solvent and a separate plasticizer.

7. A composition as claimed in claim 6, wherein the at least one bioadhesive comprises karaya gum, and wherein the separate solvent comprises a polyhydric alcohol and the separate plasticizer comprises glycerin.

8. A composition as claimed in claim 7, wherein the at least one soluble PVP is present in an amount of from 5–30 wt%, the karaya gum is present in an amount of from 10–50 wt%, the polyhydric alcohol is present in an amount of from 7–40 wt%, and the glycerin is present in an amount of from 10–50 wt%, all based on the combined weight of the at least one soluble PVP, the karaya gum, the polyhydric alcohol and the glycerin.

9. A composition as claimed in claim 7, wherein the at least one soluble PVP is present in an amount of from 7–15 wt%, the karaya gum is present in an amount of from 20–40 wt%, the polyhydric alcohol is present in an amount of from 15–35 wt%, and the glycerin is present in an amount of from 20–40 wt%, all based on the combined weight of the at least one soluble PVP, the karaya gum, the polyhydric alcohol and the glycerin.

10. A composition as claimed in claim 7, wherein the weight ratio of the at least one PVP to karaya gum is of from 1:1 to 1:7.

11. A composition as claimed in claim 7, wherein the weight ratio of the at least one PVP to karaya gum is of from 1:3 to 1:4.

12. A composition as claimed in claim 7, wherein the weight ratio of the karaya gum to glycerin is of from 10:1 to 1:2.

13. A composition as claimed in claim 7, wherein the weight ratio of karaya gum to propylene glycol is of from 10:1 to 1:1.

14. A composition according to claim 7, wherein the polyhydric alcohol comprises propylene glycol.

15. A composition as claimed in claim 1, wherein the one or more active agents is selected from the group consisting of: anesthetics, anti-inflammatories, analgesics, antimigranes, antimicrobials, dental agents, antibiotics, anorexics, polypeptide drugs, protein drugs, opioid agonists, opioid antagonists, antiemetics, antineoplastics, antiparkinsonians, antidiuretics, hormones, bronchodilators, central nervous system stimulants and agents, oxyotics, and vasodilators.

16. A composition for administration on mucous membranes of one or more active agents comprising:
    (a) a source of one or more active agents;
    (b) an adhesive layer adapted for adhering to mucosal tissue and which results from an admixture which comprises:
        (i) at least one soluble polyvinylpyrrolidone polymer (PVP);
        (ii) at least one bioadhesive; and
        (iii) optionally one or more solvents, wherein the source (a), containing the one or more active agents, includes a separate layer than the adhesive layer (b); and
    (c) a backing layer which is occlusive to the active agents and which is in contact with the separate layer.

17. A composition according to claim 16, wherein a first major surface of the adhesive layer is adjacent to and in contact with a first major surface of the separate layer.

18. A composition according to claim 17, wherein:
    (c) said backing layer which is in contact with a second major surface of the separate layer which is opposite the first major surface of the separate layer; and further comprising
    (d) a removable release liner which is in contact with a second major surface of the adhesive layer which is opposite to the first major surface of the separate layer.

19. A composition according to claim 16, wherein the source (a) includes an active agent reservoir and the adhesive layer is peripheral to the active agent reservoir.

20. A composition according to claim 16, wherein the adhesive layer includes one or more solvents, wherein said one or more solvents comprises a separate solvent and a separate plasticizer, and wherein said at least one bioadhesive comprises karaya gum.

21. A composition according to claim 20, wherein the separate solvent comprises a polyhydric alcohol, and wherein the separate plasticizer comprises glycerin.

22. A method for prolonged topical administration of one or more active agents to a subject comprising the steps of:
    (a) providing the composition of claim 1, and
    (b) contacting an area of mucous membrane with said composition to administer the one or more active agents.

23. A method for prolonged topical administration of one or more active agents to a subject comprising the steps of:
   (a) providing the composition of claim 16, and
   (b) contacting an area of mucous membrane with said composition to administer the one or more active agents.

24. A method for producing the composition according to claim 1, comprising mixing
   (a) at least one soluble polyvinylpyrrolidone polymer;
   (b) at least one bioadhesive;
   (c) a therapeutically effective amount of one or more active agents;
   (d) optionally one or more solvents, to form a composition; and
contacting said composition with a backing layer which is occlusive to said active agents.

25. A method for producing the composition according to claim 16, comprising:
   (a) forming an active agent source which comprises one or more active agents;
   (b) forming a separate adhesive layer adapted for adhering to mucosal tissue, which comprises mixing:
      (i) at least one soluble polyvinylpyrrolidone polymer;
      (ii) at least one bioadhesive; and
      (iii) optionally one or more solvents; and
   (c) contacting said adhesive layer with a backing layer which is occlusive to the active agents.

26. A method for decreasing the time required for adhesion of a composition to mucosal tissue, comprising:
   applying the composition according to claim 16 to mucosal tissue, whereby the composition adheres to the mucosal tissue substantially at the moment of contact without any additional pressure.

27. A composition as claimed in claim 1, wherein the soluble polyvinylpyrrolidone polymer has a molecular weight of about 1,000,000 to about 1,500,000.

28. A composition as claimed in claim 1, wherein the composition contains less than 3% by weight of water.

29. A device for the transmucosal delivery of one or more active agents comprising:
   (a) a mucoadhesive layer which adheres to mucosal tissue, wherein said mucoadhesive layer includes at least one soluble polyvinylpyrrolidone polymer (PVP);
   (b) an active agent layer; and
   (c) a backing layer which is occlusive to the active agents.

30. The transmucosal delivery device according to claim 29, wherein said mucoadhesive layer further includes at least one bioadhesive.

31. The transmucosal delivery device according to claim 30, wherein said bioadhesive is at least one compound selected from the group consisting of water-soluble or water-insoluble polymers, natural gums, starches, alginates, cellulose materials, and natural or synthetic polysaccharides.

32. The transmucosal delivery device according to claim 30, wherein said bioadhesive includes karaya gum.

33. The transmucosal delivery device according to claim 29, wherein said active layer includes anesthetics, anti-inflammatories, analgesics, antimigranes, antimicrobials, dental agents, antibiotics, anorexics, polypeptide drugs, protein drugs, opioid agonists, opioid antagonists, antiemetics, antineoplastics, antiparkinsonians, antidiuretics, hormones, bronchodilators, central nervous system stimulants and agents, oxyotics, vasodilators and mixtures thereof.

34. The transmucosal delivery device according to claim 29, wherein said device is in a flexible, finite form.

* * * * *